United States Patent
Kontos

[19]

[11] Patent Number: 6,024,747
[45] Date of Patent: Feb. 15, 2000

[54] DEVICE AND METHOD FOR SUTURING BLOOD VESSELS AND THE LIKE

[75] Inventor: Stavros Kontos, Woodcliff Lake, N.J.

[73] Assignee: X-Site L.L.C., Totowa, N.J.

[21] Appl. No.: 09/126,316

[22] Filed: Jul. 30, 1998

Related U.S. Application Data

[63] Continuation-in-part of application No. 08/661,844, Jun. 11, 1996, Pat. No. 5,855,585.

[51] Int. Cl.⁷ ..................................................... A61B 17/04
[52] U.S. Cl. ........................... 606/144; 606/139; 606/148
[58] Field of Search ..................................... 606/139, 144, 606/145, 146, 147, 148, 232; 112/169, 80.03

[56] References Cited

U.S. PATENT DOCUMENTS

| | | |
|---|---|---|
| 4,107,953 | 8/1978 | Casillo . |
| 4,553,543 | 11/1985 | Amarasinghe ........................ 128/334 R |
| 4,757,827 | 7/1988 | Buchbinder . |
| 4,799,495 | 1/1989 | Hawkins et al. . |
| 4,890,612 | 1/1990 | Kensey . |
| 5,108,421 | 4/1992 | Fowler . |
| 5,304,184 | 4/1994 | Hathaway et al. . |
| 5,312,360 | 5/1994 | Behl . |
| 5,312,423 | 5/1994 | Rosenbluth . |
| 5,324,306 | 6/1994 | Makower . |
| 5,336,229 | 8/1994 | Noda . |
| 5,336,231 | 8/1994 | Adair . |
| 5,383,896 | 1/1995 | Gershony et al. . |
| 5,391,183 | 2/1995 | Janzen et al. . |
| 5,417,699 | 5/1995 | Klein et al. . |
| 5,431,666 | 7/1995 | Sauer et al. . |
| 5,437,631 | 8/1995 | Janzen . |
| 5,447,502 | 9/1995 | Haaga . |
| 5,474,543 | 12/1995 | McKay . |
| 5,527,322 | 6/1996 | Klein et al. . |
| 5,578,044 | 11/1996 | Gordon et al. . |
| 5,613,974 | 3/1997 | Andreas et al. . |
| 5,676,689 | 10/1997 | Kensey . |
| 5,728,133 | 3/1998 | Kontos . |
| 5,855,585 | 1/1999 | Kontos . |
| 5,868,762 | 2/1999 | Cragg et al. ............................. 606/144 |

FOREIGN PATENT DOCUMENTS

| | | |
|---|---|---|
| 0 637 431 | 2/1995 | European Pat. Off. . |
| 95/13021 | 5/1995 | WIPO . |

*Primary Examiner*—Michael Buiz
*Assistant Examiner*—Tina T. D. Pham
*Attorney, Agent, or Firm*—Kenyon & Kenyon

[57] ABSTRACT

A method and device for sealing an opening in an anatomical structure within a living body includes an elongated member that is partially inserted into an anatomical structure such as a blood vessel. The inserted portion holds a plurality of needles, which are connected to a suture that travels through and out of the device. When the suture is pulled and drawn through the device, the needles are pulled through the vessel wall on opposite sides of the opening. The needles may alternatively be attached to a platform that engages the guide wire, the guide wire being utilized to deploy the needles. Once the needles are drawn fully through the vessel wall, the suture can be separated from the needles and knotted to seal the opening. Alternatively, the suture may be crimped using a crimping device. The device may also include a body designed to receive the needles.

11 Claims, 44 Drawing Sheets

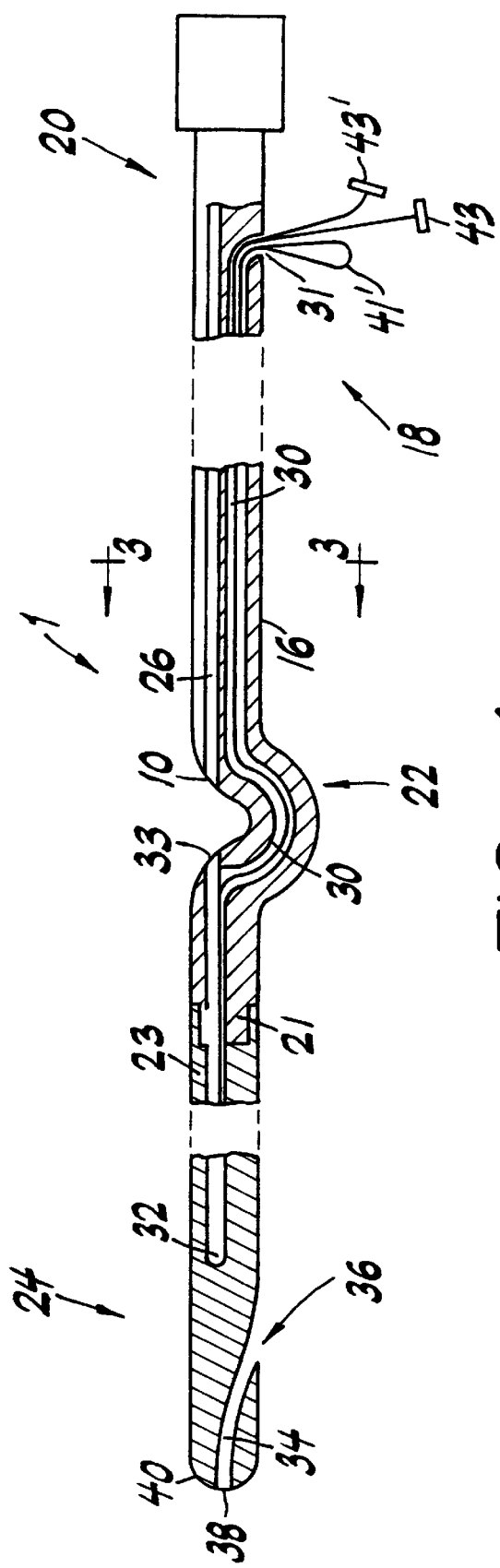

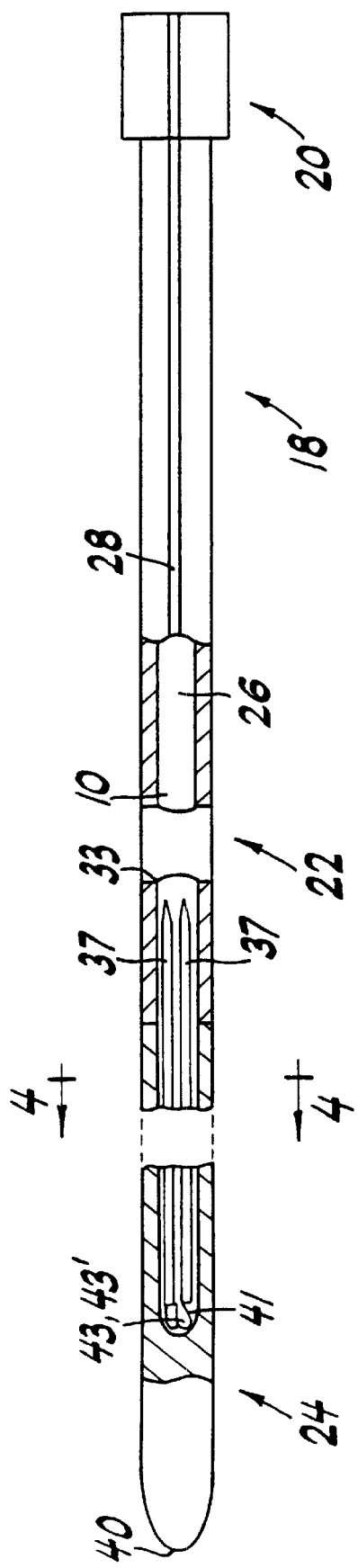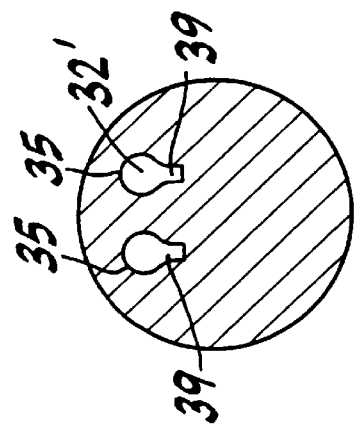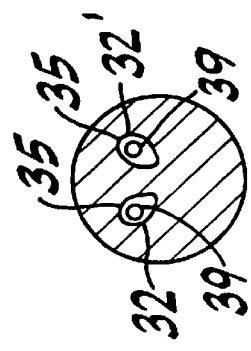

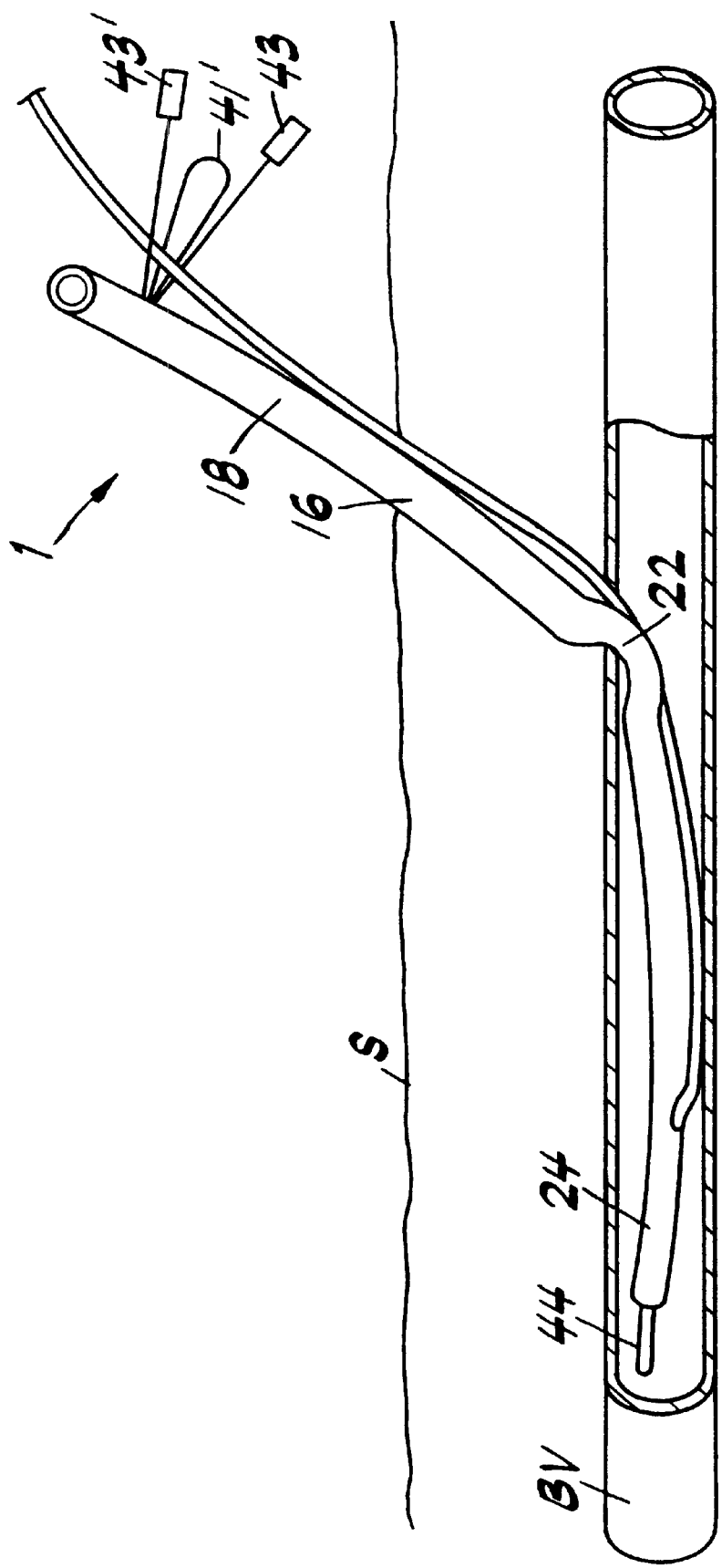

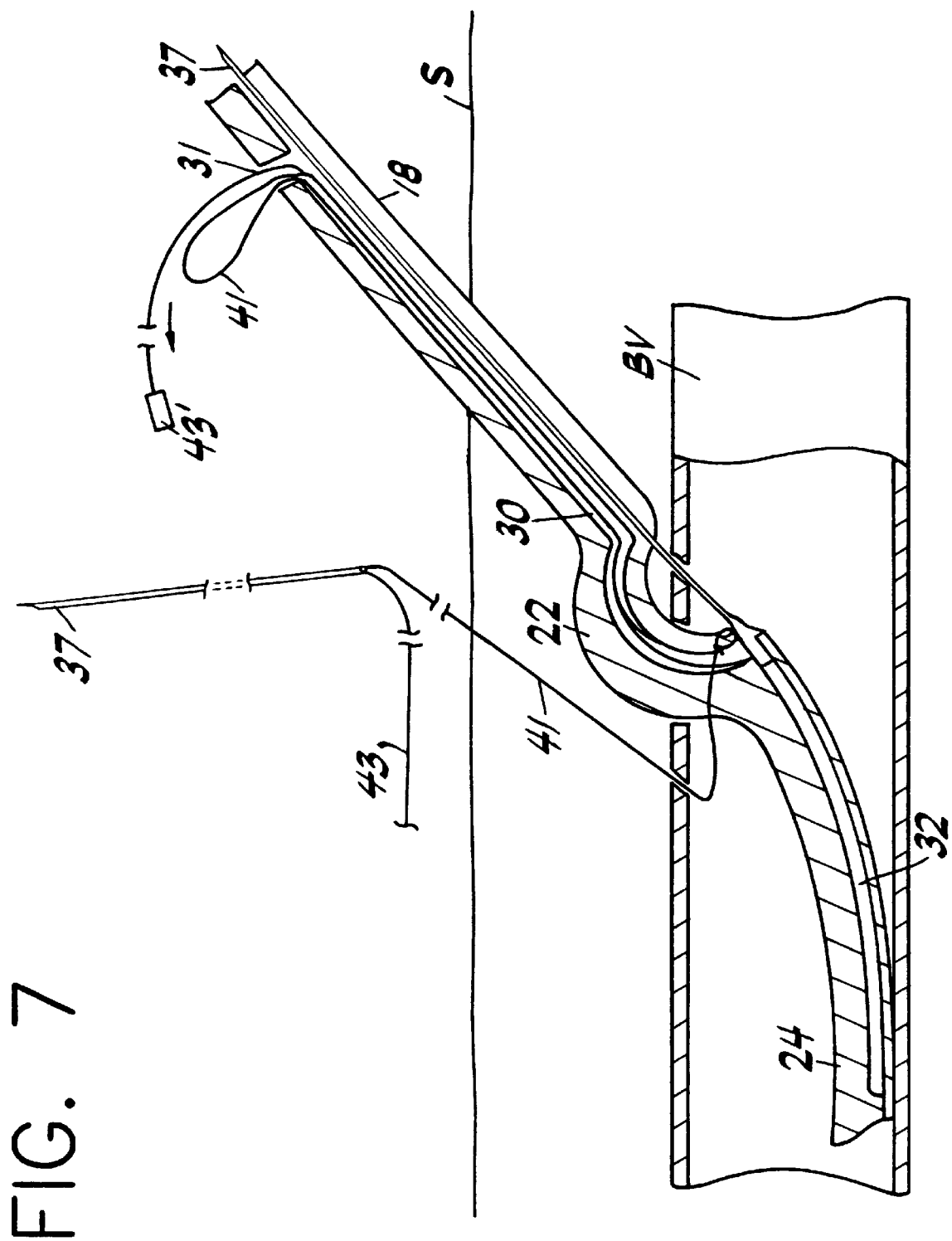

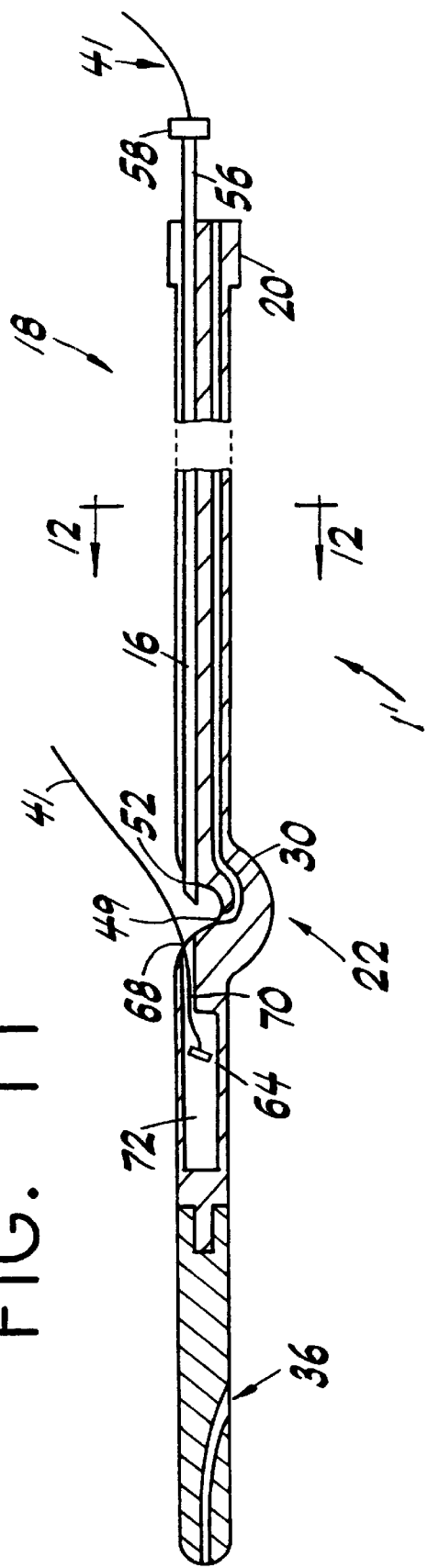

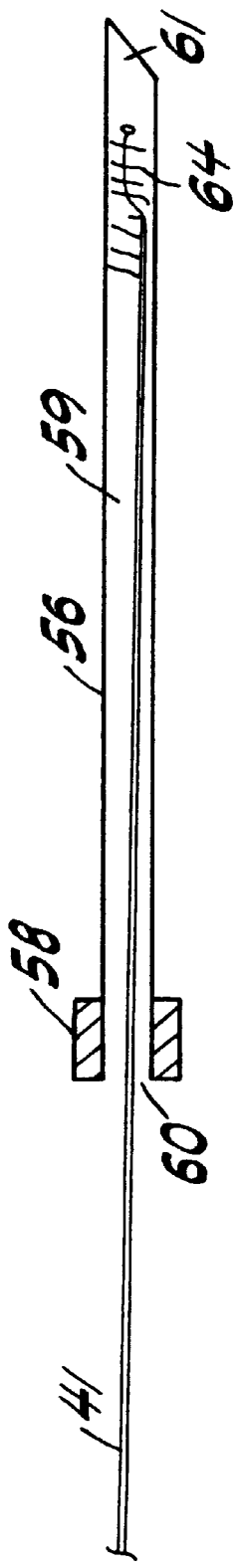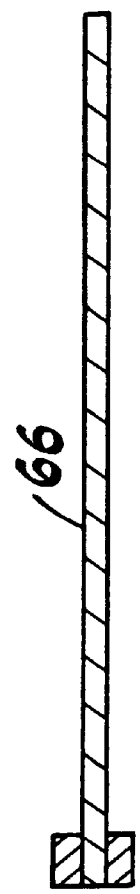
FIG. 13
FIG. 14

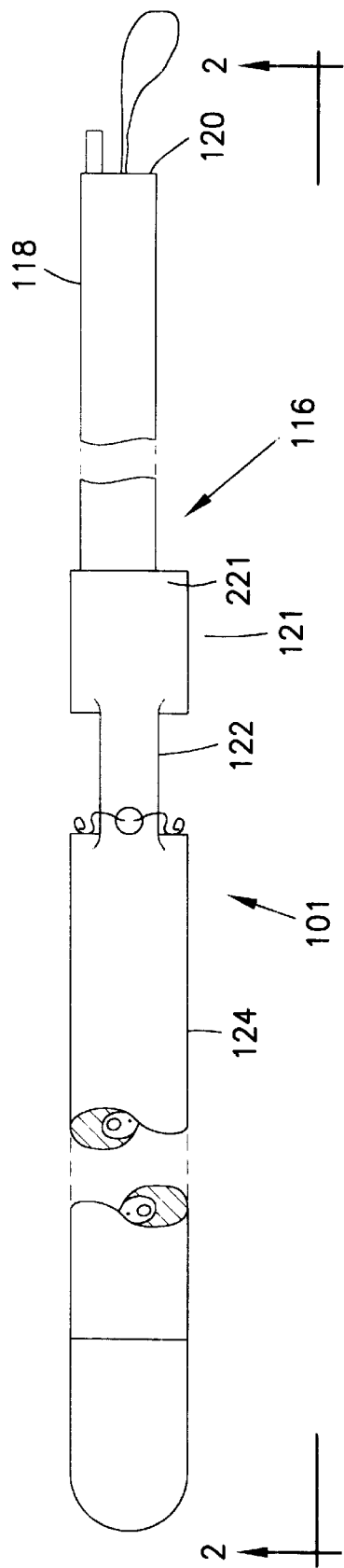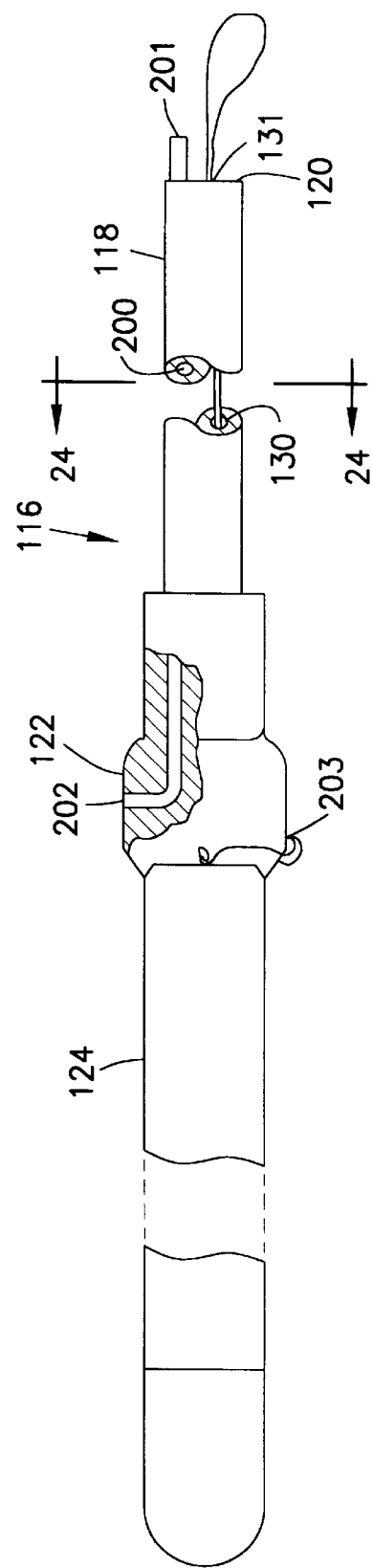

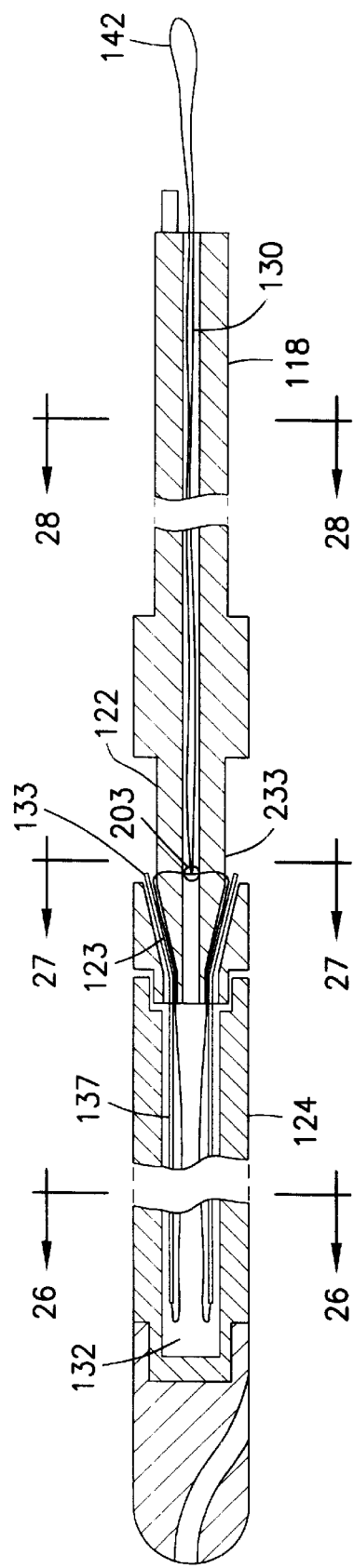
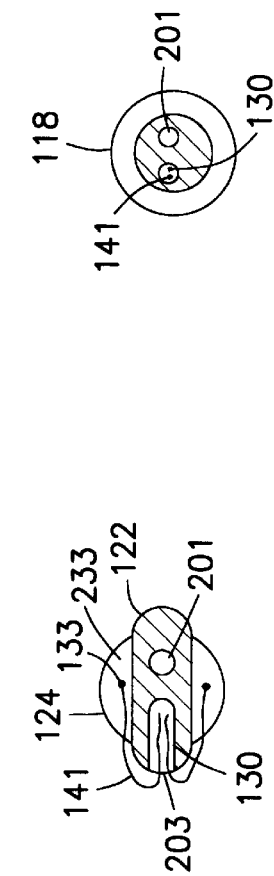
Fig. 25
Fig. 27
Fig. 28
Fig. 26

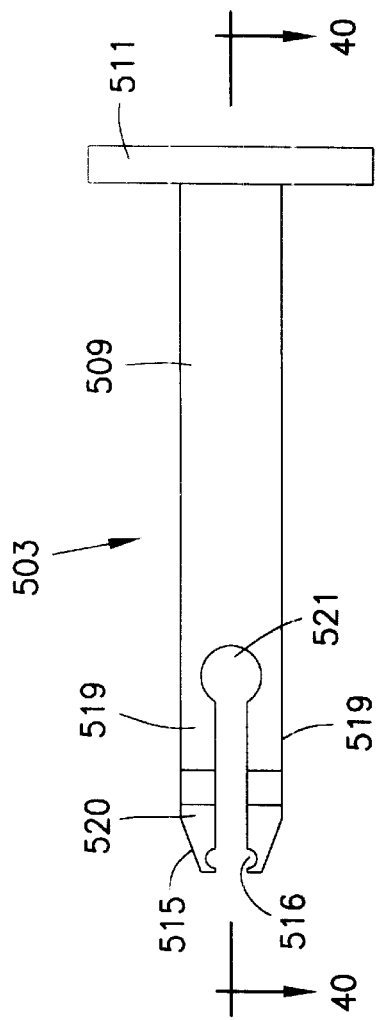
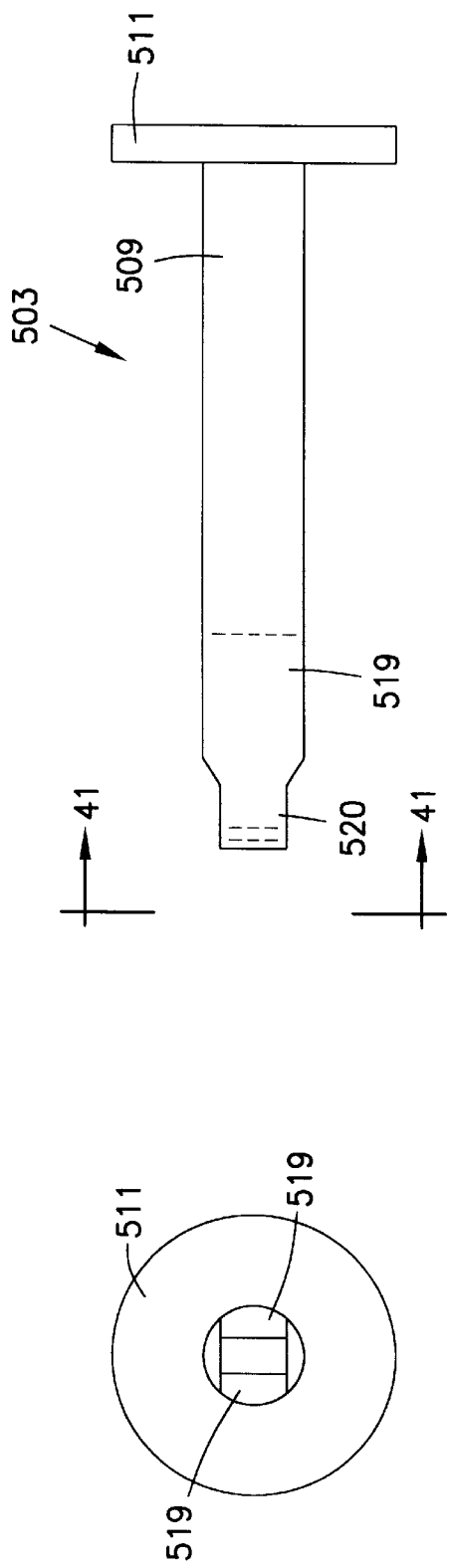

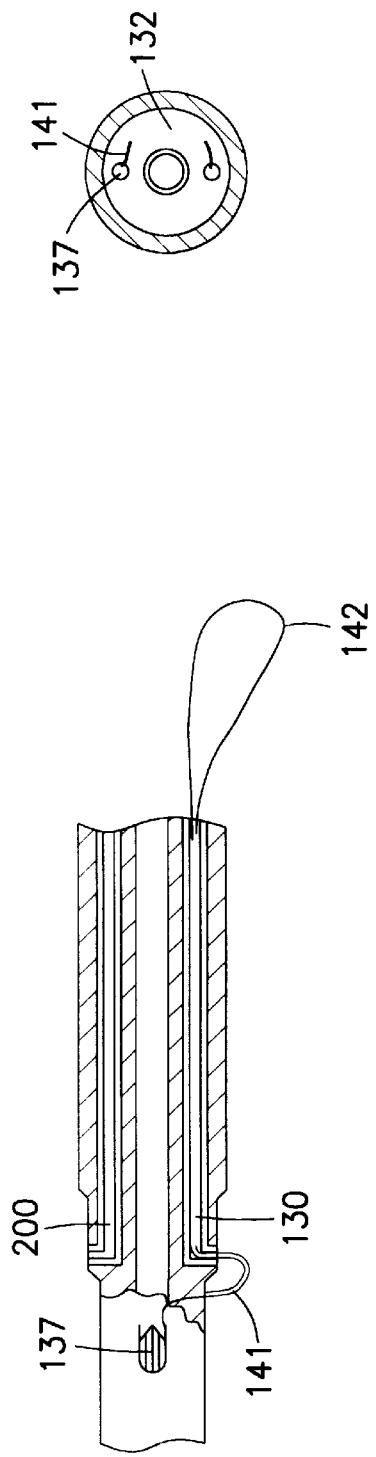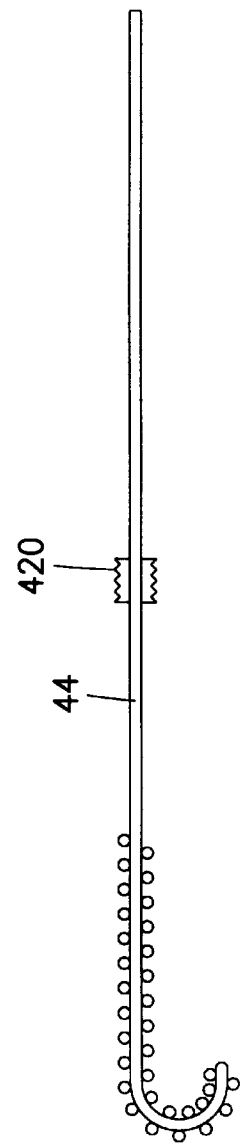

DEVICE AND METHOD FOR SUTURING BLOOD VESSELS AND THE LIKE

This application is a continuation-in-part of U.S. patent application Ser. No. 08/661,844, filed Jun. 11, 1996, now U.S. Pat. No. 5,855,585.

FIELD OF THE INVENTION

The present invention relates generally to surgical instruments, and more specifically to devices for the suturing of punctures in blood vessels, internal organs and internal tissues accessed via a tissue tract.

BACKGROUND OF THE INVENTION

Many surgical procedures require the insertion of catheters and/or surgical devices into blood vessels and other internal structures. For example, in the treatment of vascular disease, it is often necessary to insert an instrument, i.e., a catheter, into the blood vessel to perform the treatment procedure. Such treatment procedures often involve piercing a wall of the blood vessel, inserting an introducer sheath into the blood vessel via the opening, and maneuvering the procedural catheter through the introducer sheath to a target location within the blood vessel. Of course in order to complete such a procedure, the sides of the opening in the wall of the blood vessel must be sealed to prevent bleeding while facilitating healing of the wound. At present, this sealing is commonly accomplished by application of direct pressure over the puncture site by a physician or other trained medical professional. Due to the dangers of thrombosis, the substantial reduction of blood flow through the blood vessel due to the application of pressure is undesirable and potentially dangerous to the patient. In addition, the procedure is extremely time consuming; often requiring that pressure be applied for forty-five minutes or more to achieve acceptable sealing.

Other sealing techniques include the application of a biogenic sealing material over the opening to seal the wound. However, proper placement of the sealing material is difficult to achieve and, the plug of sealing material left inside the blood vessel may result in serious health risks to the patient.

As a result, devices have been developed which are inserted through the puncture in order to suture openings created in blood vessels. However, these devices suffer from various drawbacks.

For example, U.S. Pat. No. 5,417,699 to Klein et al. describes a device wherein two needles coupled to a distal end of an insertion shaft are surrounded by an outer sheath during insertion into an internal structure. Once inside the internal structure, the outer sheath is withdrawn and bowed sections of the needles, which had been constrained within the outer sheath against an outward spring bias, deploy away from the insertion shaft. The insertion shaft is then withdrawn drawing the needles through the walls of the internal structure. The arcuate shape of the needles is intended to bring the needles back along a curved path toward the insertion shaft so that the free ends of the needles may be captured on the shaft and the device withdrawn from the body. Thereafter, the distal ends of the needles must be detached from the insertion shaft so that a length of suture extending between distal ends of the two needles may be drawn through the walls of the internal structure to seal the opening.

However, the curved shape of the proximal ends of the needles of this device requires an insertion sheath of increased diameter. Thus, after withdrawal of a treatment catheter from an opening formed in an internal structure, insertion of the increased diameter outer sheath of the device of Klein et al. actually expands the opening in the wall of the internal structure. In addition, the device of Klein et al. employs several slidably mounted concentric shafts and mechanisms for the deployment and capture of the needles which make the device costly to manufacture and cumbersome to operate.

SUMMARY OF THE INVENTION

The present invention is directed to a device for sealing an opening in an anatomical structure within a living body. The device includes a flexible tube including a proximal portion extending along an axis coupled to a distal portion extending along the axis by a central portion, wherein the central portion extends away from the axis to form a gap between a distal end of the proximal portion and a proximal end of the distal portion. A needle retention channel formed within the distal portion for holding a plurality of needles therein extends along the axis to an opening formed in the proximal end of the distal portion. In addition, a needle receiving channel formed within the proximal portion extends along the axis to an opening formed in the distal end of the proximal portion. Finally, a lumen extends from an opening formed in the end of the proximal portion to the needle retention channel. Thus, when the device is in an operative position, the flexible tube extends through the opening in the anatomical structure with the opening in the distal end of the proximal portion and the opening in the proximal portion on opposite sides of the anatomical structure.

The present invention is also directed to a method including the steps of guiding into an opening in an anatomical structure, a device including a substantially linear proximal and distal portions extending along a common axis and a curved central portion coupling the proximal and distal portions so that a gap is formed therebetween. The device is positioned so that the curved central portion is within the opening with a needle retention channel opening on a distal side of the anatomical structure and a needle receiving channel opening on a proximal side of the anatomical structure. The doctor then draws a pull cord attached to a distal end of a first needle out to bring a first needle proximally out of the needle retention channel through the anatomical structure and through the needle receiving channel to bring a first end of the suture through the anatomical structure. Thereafter, the device is rotated to a second desired position so that a second portion of the anatomical structure adjacent to the opening is located within the gap and a pull cord attached to a distal end of a second needle is drawn to bring the second needle proximally out of the needle retention channel through the anatomical structure and into the needle receiving channel so that the second end of the suture is drawn through the anatomical structure. The first and second ends of the suture are then secured together to seal the opening.

A further embodiment of the invention is directed to a surgical stitching device comprising a flexible tube including substantially linear proximal and distal portions defining an axis and a curved central portion coupling the proximal and distal portions so that a gap is formed therebetween. A puncture needle channel extends through the proximal portion along the axis to an opening formed in the distal end of the proximal portion, while a puncture needle receiving channel extends through the distal portion along the axis to a suture retention channel of relatively larger cross-sectional area. A puncture needle including a central lumen is slidably received in the puncture needle channel so that, by applying pressure to a proximal end of the puncture needle, a user may manually move the puncture needle out of the opening formed in the distal end of the puncture needle channel, across the gap and into the puncture needle retention channel until a distal end of the puncture needle is received within the suture retention chamber. A piston is slidably received in the central lumen so that, when the distal end of the puncture needle is received within the suture retention chamber, a user may move the piston distally through the central lumen to release the contents of the central lumen into the suture retention chamber.

Another embodiment of the device according to the present invention allows simultaneous deployment of multiple puncture needles. The device includes, for example, a tubular member including a proximal portion having a suture lumen and a position indication lumen extending therethrough and a distal portion having, for example, a pair of needle channels extending from a single needle chamber to a pair of openings in the proximal end of the distal portion. The distal channel holds, for example, a pair of needles, which extend from the needle chamber to respective needle channels. The proximal portion and the distal portion are both, for example, generally circular in cross-section, and the proximal and distal portions are connected by a central portion having, for example, an oblong cross-section. The central portion has, for example, a suture opening connected to the suture lumen of the proximal portion. The device according to this embodiment of the present invention also includes a needle receiving body, having an annular cross-section, which fits around the proximal portion. The needle receiving body has, for example, a pair of axially-running puncture needle receiving lumens extending fully therethrough from two openings on a distal end of the needle receiving body to two openings on the proximal end. The openings on the distal end of the needle receiving body are aligned, for example, with the openings on the proximal end of the distal portion. The ends of a length of suture are each connected to a distal end of one of the needles. The length of suture extends from the distal ends of the needles, through the needle retention channels, the central portion (via the suture opening), and the suture lumen, and exits the device from an opening on the proximal end of the proximal portion. With the device inserted so that the distal portion of the device is inside the anatomical structure, the length of suture is drawn from the device. The ends of the length of suture simultaneously pull the needles out of the needle chamber and the needle channels, through the walls of the anatomical structure, and into the needle receiving lumens in the needle receiving body. The suture may then be separated from the needles and the ends secured together to seal the opening.

In a further arrangement, a device according to the present invention may include a guide lumen for the guide wire. The needles may be grounded in a platform, the platform engaging a fitting on the guide wire. The guide wire itself may then be manipulated to deploy the needles.

The present invention also includes a knot pusher. The knot pusher is shaped, for example, as a longitudinal member having a widened proximal end for ease of holding and a rounded distal end. The distal end includes a longitudinal slit extending from the distal end of the knot pusher. The slit has a constant width throughout its length. The radial depth of the slit, however, decreases as the slit extends away from the distal end, tapering to zero at a point along the length of the knot pusher. The face of the distal end of the knot pusher also has a circular recess with a diameter wider than the width of the longitudinal slit. A knot tied in a length of suture will fit into the recess, but only the ends of the length of suture will fit into the slit. The operator may therefore draw the length of suture through the slit, thereby bringing the knot closer to the opening in the anatomical structure and eventually sealing the opening in the anatomical structure.

Alternatively, the suture may be stabilized using a crimping device according to the present invention. The crimping device includes a piston and barrel, the piston having a compressible distal end (for example a pair of arms). The distal ends of the piston and barrel include camming surfaces that compress the distal end of the piston when it is inserted into the barrel. The distal end of the piston is constructed to receive a grommet, which is crimped when the piston is compressed. The suture is threaded through the grommet prior to crimping, and the grommet, when crimped, clamps the suture and retains it in place.

BRIEF DESCRIPTION OF THE DRAWINGS

FIG. 1 shows a side view of a cross-section of a suturing device according to a first embodiment of the invention;

FIG. 2 shows a top view of a cross-section of a suturing device according to the first embodiment of the invention;

FIG. 3A shows a cross-section of a device according to the first embodiment of the invention taken along line 3—3 of FIG. 1;

FIG. 3B shows an alternative cross-section of a device according to the first embodiment of the invention taken along line 3—3 of FIG. 1;

FIG. 4A shows a cross-section of a device according to the first embodiment of the invention taken along line 4—4 of FIG. 2;

FIG. 4B shows an alternative cross-section of a device according to the first embodiment of the invention taken along line 4—4 of FIG. 2;

FIG. 6A shows a partially cross-sectional view of the blood vessel with a device according to the first embodiment of the present invention received on the guide wire in a first desired position;

FIG. 7 shows a partially cross-sectional view of the blood vessel with a device according to the first embodiment of the present invention in a second desired position;

FIG. 11 shows a side view of a cross-section of a suturing device according to a second embodiment of the invention;

FIG. 12 shows a cross-section of a device according to the second embodiment of the invention taken along line 12—12 of FIG. 11;

FIG. 13 shows a cross-sectional view of a puncture needle according to the second embodiment of the present invention;

FIG. 14 shows a side view of a plunger according to the second embodiment of the present invention;

FIG. 22 shows a side view of a fifth embodiment of the suture device according to the present invention;

FIG. 23 shows a side view of the suture device of FIG. 22, with the device rotated 90° from the position shown in FIG. 22;

FIG. 25 shows a side view of the suture device of FIG. 22;

FIG. 26 shows a cross-sectional view of the suture device of FIG. 25 taken along the line 26—26;

FIG. 27 shows a cross-sectional view of the suture device of FIG. 25 taken along the line 27—27;

FIG. 28 shows a cross-sectional view of the suture device of FIG. 25 taken along the line 28—28;

FIG. 39 shows a side view of a piston according to the present invention;

FIG. 40 shows a side view of the piston of FIG. 39 taken along line 40—40 of FIG. 39;

FIG. 41 shows a front view of the piston of FIG. 39 taken along line 41—41 of FIG. 40;

FIG. 56 shows a partial cross-sectional side view of the suture device of FIG. 55 taken along line 56—56 of FIG. 55;

FIG. 57 shows a cross-sectional view of the suture device of FIG. 55 taken along ling 57—57 of FIG. 55;

FIG. 59 shows a side view of an exemplary guide wire according to the present invention;

DETAILED DESCRIPTION OF THE INVENTION

Figure 5:
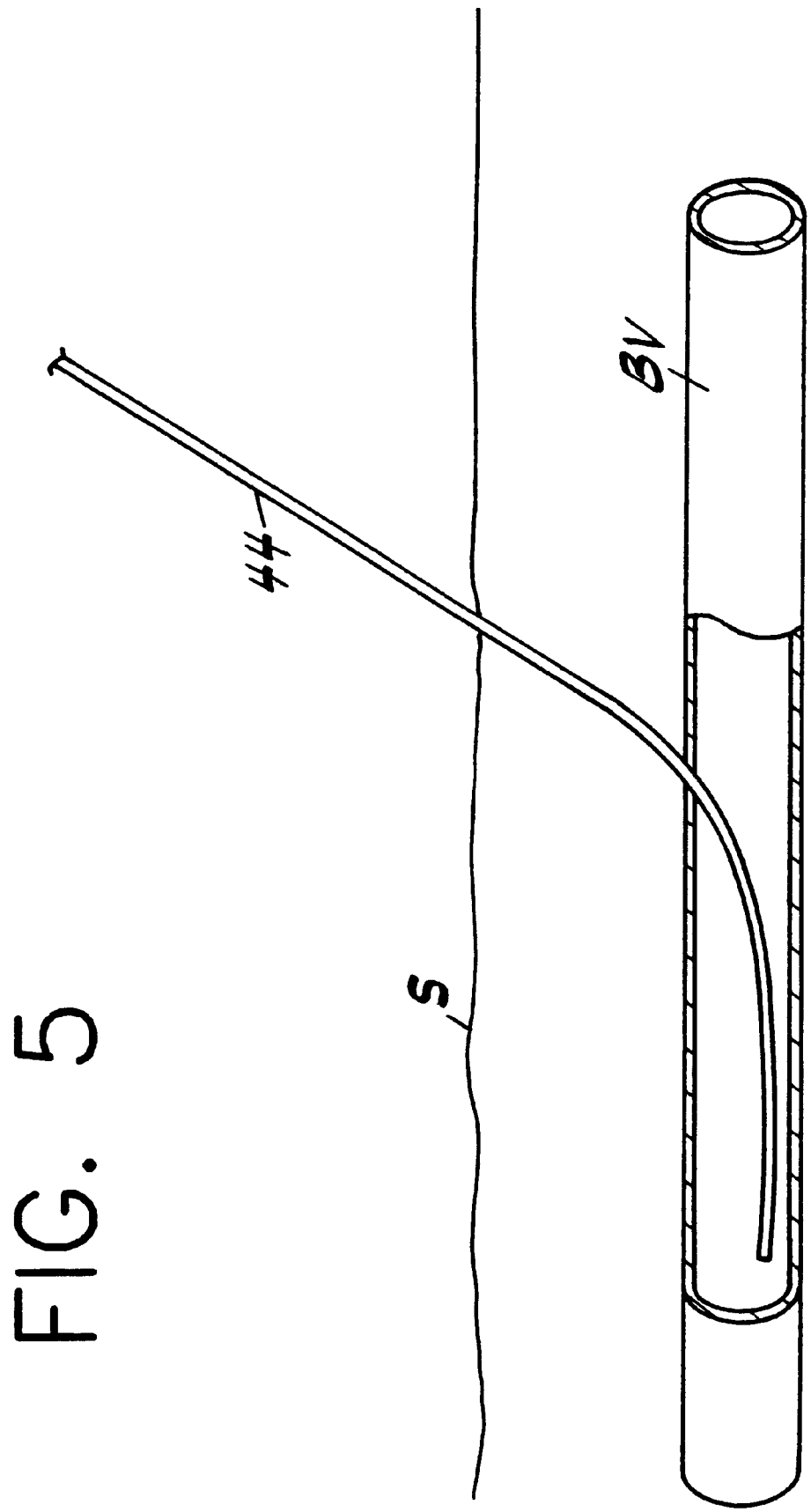
FIG. 5 shows a partially cross-sectional view of a blood vessel within a body with a guide wire inserted therein.

Referring now to the drawings, in which like reference numerals identify similar or identical elements, FIGS. 1–8 show a device 1 according to a first embodiment of the invention for suturing punctures in blood vessels, internal organs and the like. The device 1 includes flexible tube 16 of substantially circular cross-section, which has a proximal part 18 and a distal part 24. The proximal part 18 extends from a first end 20 through a central arcuate portion 22 to a second end 21 which mates with a proximal end 23 of the distal part 24. The central arcuate portion may preferably be substantially circular with a radius of from 0.100" to 0.600". The flexible tube 16 is preferably constructed of a thermoplastic such as polyurethane, polyethylene, or the like, in two or three parts bonded together. The various parts of the flexible tube 16 may preferably be either extruded or molded. Those skilled in the art will recognize that it will be more economical to extrude the parts including one or two lumens, while the more complex, and curved sections of the flexible tube 16 may be molded. The length of the flexible tube may be selected to fit the requirements of a particular situation and is preferably between 1" and 16" in length.

The flexible tube 16 includes a large interior needle withdrawal lumen 26 which extends through the proximal part 18 from the first end 20 to an opening 10 at a proximal end of the central arcuate portion 22. As seen in FIGS. 3A and 3B, the needle withdrawal lumen 26 may preferably be oval in cross-section and may include an optional slot 28 opening to the outside of the flexible tube 16.

In addition, a flash back lumen 30 extends from an opening 31 formed in the proximal part 18 through the central arcuate portion 22 to open into two needle retention bores 32 and 32' formed side-by-side in the distal part 24. As seen in FIG. 3A, the flash back lumen 30 may be circular in cross-section and is sized to simultaneously accommodate two strands of the suture 41 and the two pull cords 43 and 43'. However, as shown in FIG. 3B, the cross-section of the flash back lumen 30 may preferably include side-by-side hemispherical channels 45 and 45' for receiving the loop 41' of the suture 41 and the two pull cords 43 and 43'. This helps to ensure that the second needle 37 is not accidentally drawn out of the needle retention bore 32' when the first 37 is being pulled out. The needle retention bores 32 and 32' extend from distal ends to openings 33 and 33', respectively, formed at a position in the distal end of the central arcuate portion 22 opposite the opening 10. In addition, a substantially straight stiffening member may be inserted into the flash back lumen 30 in order to straighten the central arcuate portion 22 during insertion of the device 1 into the body. Alternatively, the device 1 may be made straight and, after insertion into the body, a curved stiffening member may be inserted to bend the device 1 thereby creating the central arcuate portion 22.

As seen in FIGS. 4A and 4B, the retention bores 32 and 32' have cross-sectional shapes including first portions 35, each shaped to receive a needle 37 and second portions 39, each shaped to receive a suture 41 and pull cord 43 or 43'. The first portions 35 are shaped to correspond to the cross-section of the needles 37 which in the preferred embodiment is substantially circular. The second portions 39, which are of reduced size so that the needles 37 are unable to enter, may be either rectangular or triangular projections extending from the first portions 35 and are sufficiently large to simultaneously accommodate the suture 41 and one of the pull cords 43 and 43'. The suture 41, which will preferably be in the range of 0.004" to 0.010" in diameter and from 15" to 35" in length, may be formed of either "reabsorbable" or "non-reabsorbable" material, as is well known in the art. The pull cords 43 and 43' will preferably be formed of non-reabsorbable material and will be of similar diameter to the suture 41. Those skilled in the art will recognize that the function of the pull cords 43 and 43' may be filled by a loop 41' of the suture 41 coupled between the distal ends of the needles 37 extended through the flash back lumen 30 so that, when the loop 41' of the suture 41 is extended proximally, the needles 37 are urged proximally through the needle retention bores 32 and 32'.

As the device 1 according to the first embodiment includes a single pair of needles, this device should preferably be used to close punctures of 9.0 French size and smaller (each French size representing 0.13" in diameter). The flexible tube 16 will, therefore, preferably be 6.0 or 8.0 French size. As described below in reference to further embodiments of the invention, devices employing two or more pairs of needles 37 may be employed to close punctures larger than 9.0 French size. Each of the needles 37 may preferably be constructed of stainless steel, be between 2" and 8" in length and have a diameter between 0.010" and 0.030".

When the device 1 is in an operative configuration, the suture 41 extends between the distal ends of two needles 37 received in the needle retention bores 32 and 32'. In the first embodiment of the invention, optional pull cords 43, 43' extend from the distal end of each of the needles 37 through the second portions 39 of the needle retention bores 32 and 32', via the flash back lumen 30, to the opening 31. However, the suture 41 may, alternatively, extend from the distal ends of the needles 37 through the second portions 39 of the needle retention bores 32 and 32', via the flash back lumen 30, to the opening 31 so that a portion of the suture loop 41' which extends out from the opening 31 may provide the function of the pull cords 43 and 43', as described below.

Finally, a guide wire lumen 34 extends through the distal part 24 of the device 1 from a proximal opening 36 to a distal opening 38 formed in a second end 40 of the device 1.

In operation, as shown in FIGS. 5–10, when an invasive procedure is performed on a patient which requires the insertion of a catheter into a blood vessel (or other structure within the body), an introducer sheath is inserted through the skin (S) into the patient's body through a puncture (P) in a wall of the blood vessel (BV). A guide wire 44 is inserted through the puncture to a target area within the blood vessel and a catheter is inserted through the introducer sheath, along the guide wire 44, to a target area within the blood vessel. After the procedure is complete, the catheter and the introducer sheath are withdrawn and the guide wire 44 is left in place. A proximal end of the guide wire 44 is then inserted through the guide wire lumen 34 and the device 1 is inserted into the body and moved along the guide wire 44 through the puncture until the central arcuate portion 22 straddles a portion of the blood vessel wall adjacent to the puncture.

By observing the flash back lumen 30 and the needle withdrawal lumen 26, the doctor may determine when the device 1 is in the desired position. Specifically, when the device 1 is inserted far enough into the blood vessel, blood will be observed in the flash back lumen 30. However, if blood is observed in the needle withdrawal lumen 26, the doctor knows that the device 1 has been inserted too far into the blood vessel.

As the device 1 is inserted into the blood vessel, the flexible tube 16 bends so that the device 1 is received within, and extends in the direction of the blood vessel without straining the vessel. In this position, the openings 33 and 33' are on the distal side of the puncture facing the opening 10 which is located on the proximal side of the puncture.

Figure 6B:
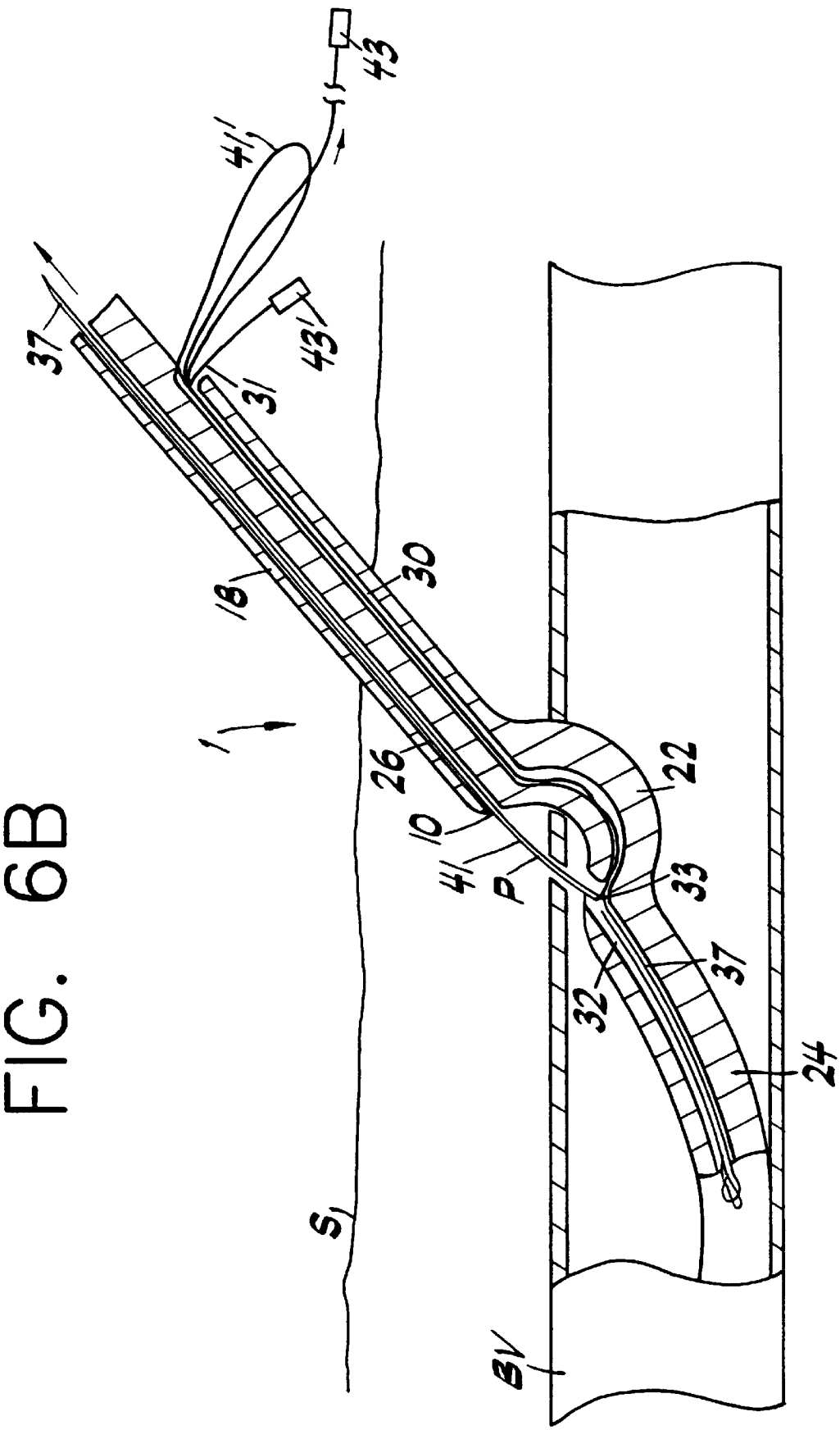
FIG. 6B shows a partially cross-sectional view of the blood vessel with the device as shown in FIG. 6A wherein a needle has been drawn through the body tissue received in the central gap.

As shown in FIG. 6B, the doctor then rotates the device 1 into a desired orientation and draws the pull cord 43 out of the opening 31, thus drawing one of the needles 37 forward through the needle retention bore 32 so that a pointed, proximal end of the needle 37 is drawn through the wall of the blood vessel, enters the opening 10 and extends into the needle withdrawal lumen 26. The needle 37 is then withdrawn through the needle withdrawal lumen 26, drawing a first end of the suture 41 through the wall of the blood vessel and into the needle withdrawal lumen 26. The needle 37 is drawn forward by means of the pull cord 43 until a proximal end of the needle 37 protrudes from the proximal end of the needle withdrawal lumen 26. The proximal end of the needle 37 is then grasped by the doctor and withdrawn from the needle withdrawal lumen 26. In order to ensure that the needles 37 will extend through the needle withdrawal lumen 26, the needles 37 will preferably be at least 4" in length.

Thereafter, the doctor rotates the device 1, as shown in FIG. 7, until the central arcuate portion 22 straddles the blood vessel wall in a desired position relative to the point at which the first end of the suture 41 penetrated the blood vessel wall. Those skilled in the art will understand that this "desired position" will usually be on the opposite side of the puncture, so that the device 1 will be rotated approximately 180° after the first needle 37 is withdrawn. When the device 1 is in the second desired orientation, the doctor draws the pull cord 43' out of the opening 31 thereby urging the second needle 37 forward through the needle retention bore 32' so that the pointed, proximal end of the second needle 37 is drawn through the wall of the blood vessel, enters the opening 10 and extends into the needle withdrawal lumen 26. The second needle 37 is withdrawn through the needle withdrawal lumen 26, drawing the second end of the suture 41 through the wall of the blood vessel and into the needle withdrawal lumen 26 as described above.

Figure 8:
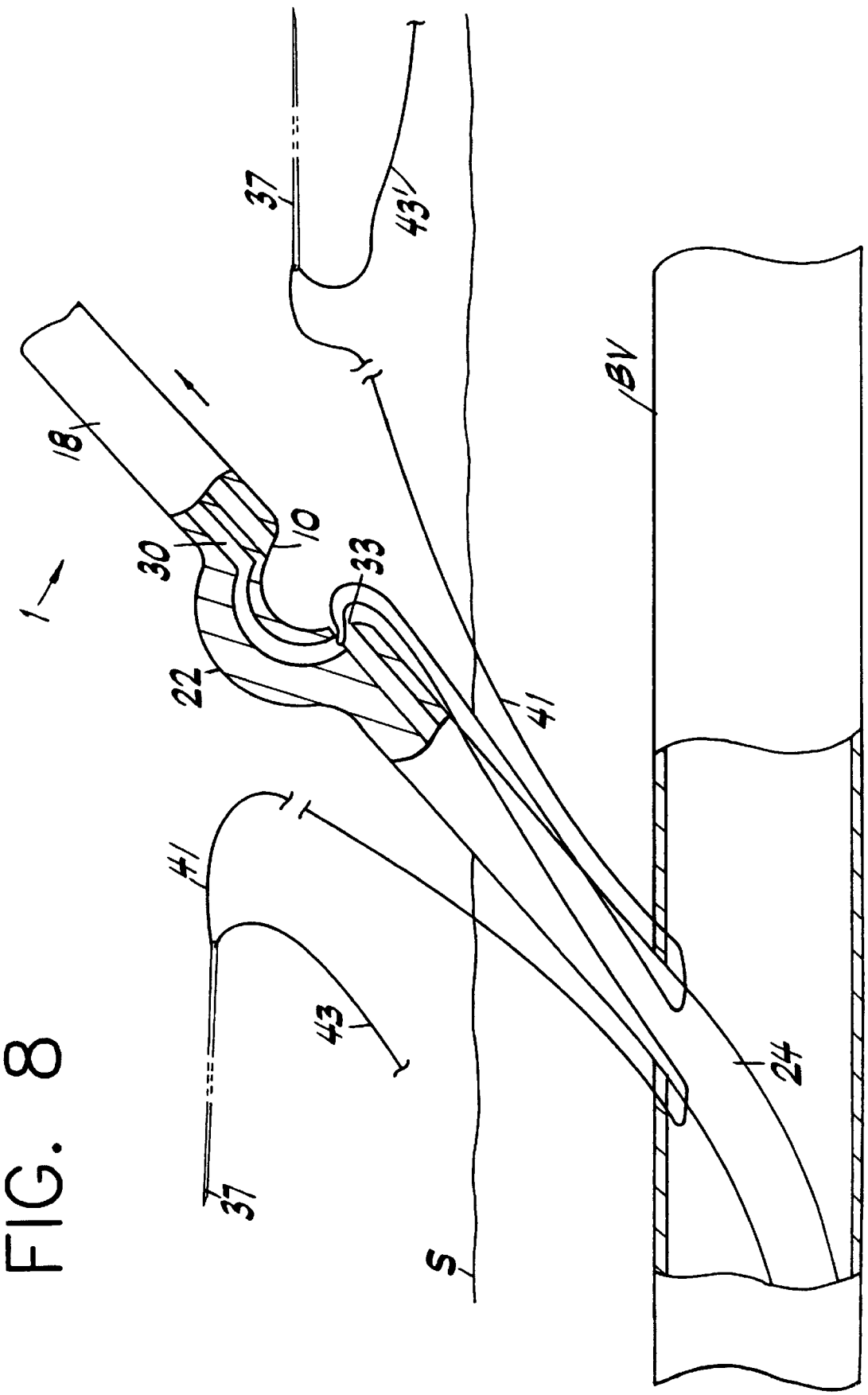
FIG. 8 shows a partially cross-sectional view of the blood vessel with a device according to the first embodiment of the present invention partially removed from the blood vessel.
Figure 9:
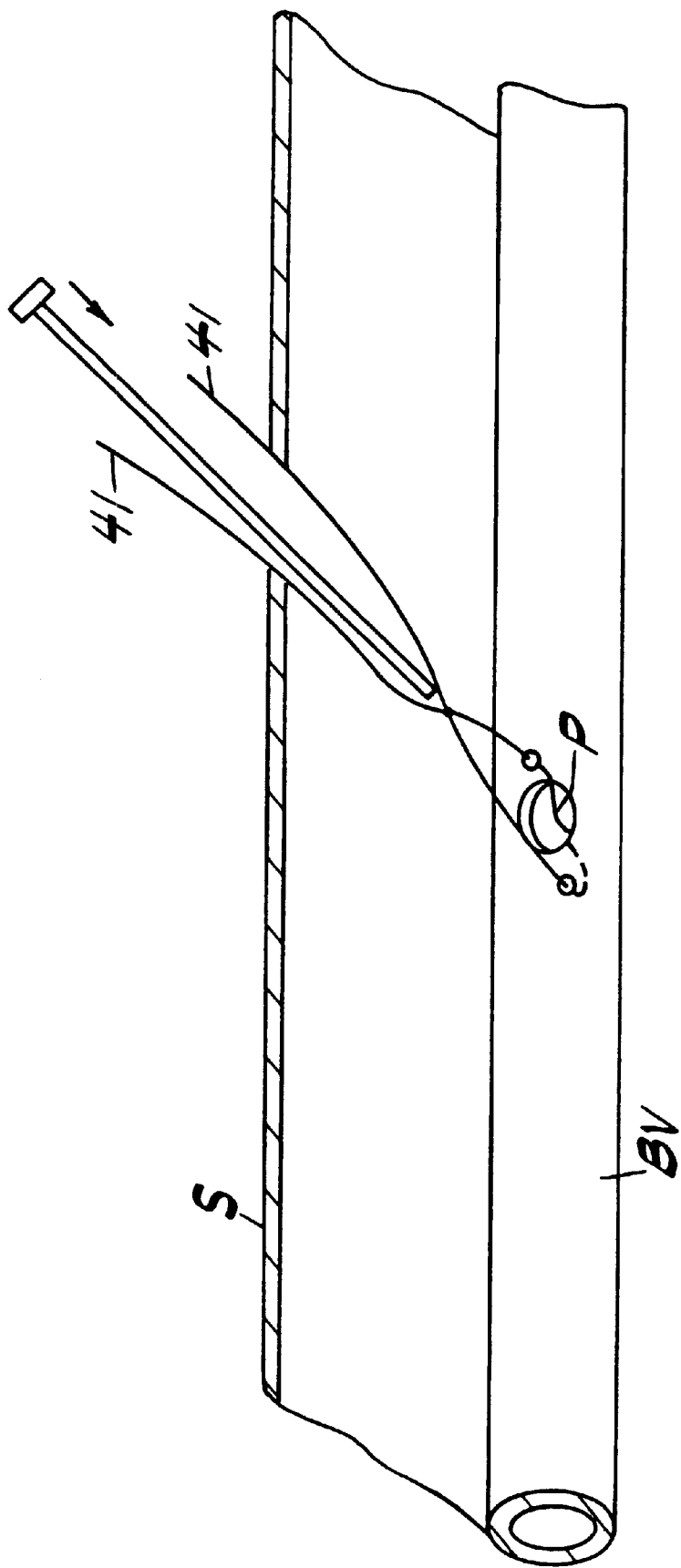
FIG. 9 shows a slip knot tied in a suture loop extending through the wall of the blood vessel being urged toward the blood vessel.
Figure 10:
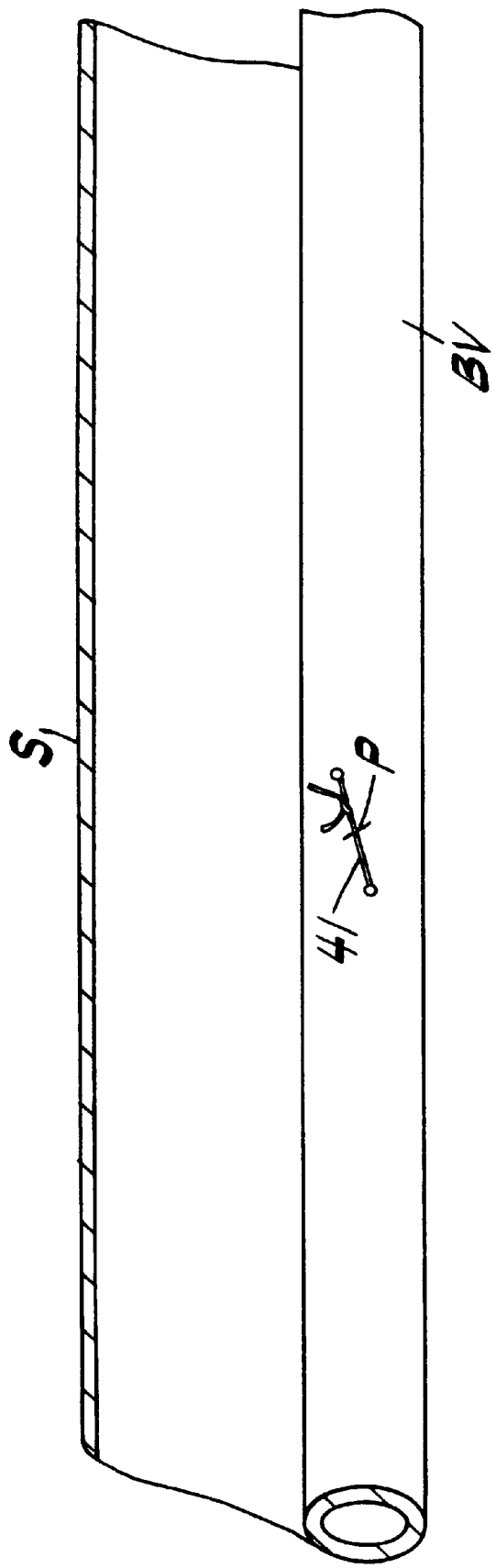
FIG. 10 shows a suture sealing the puncture.
Figure 15:
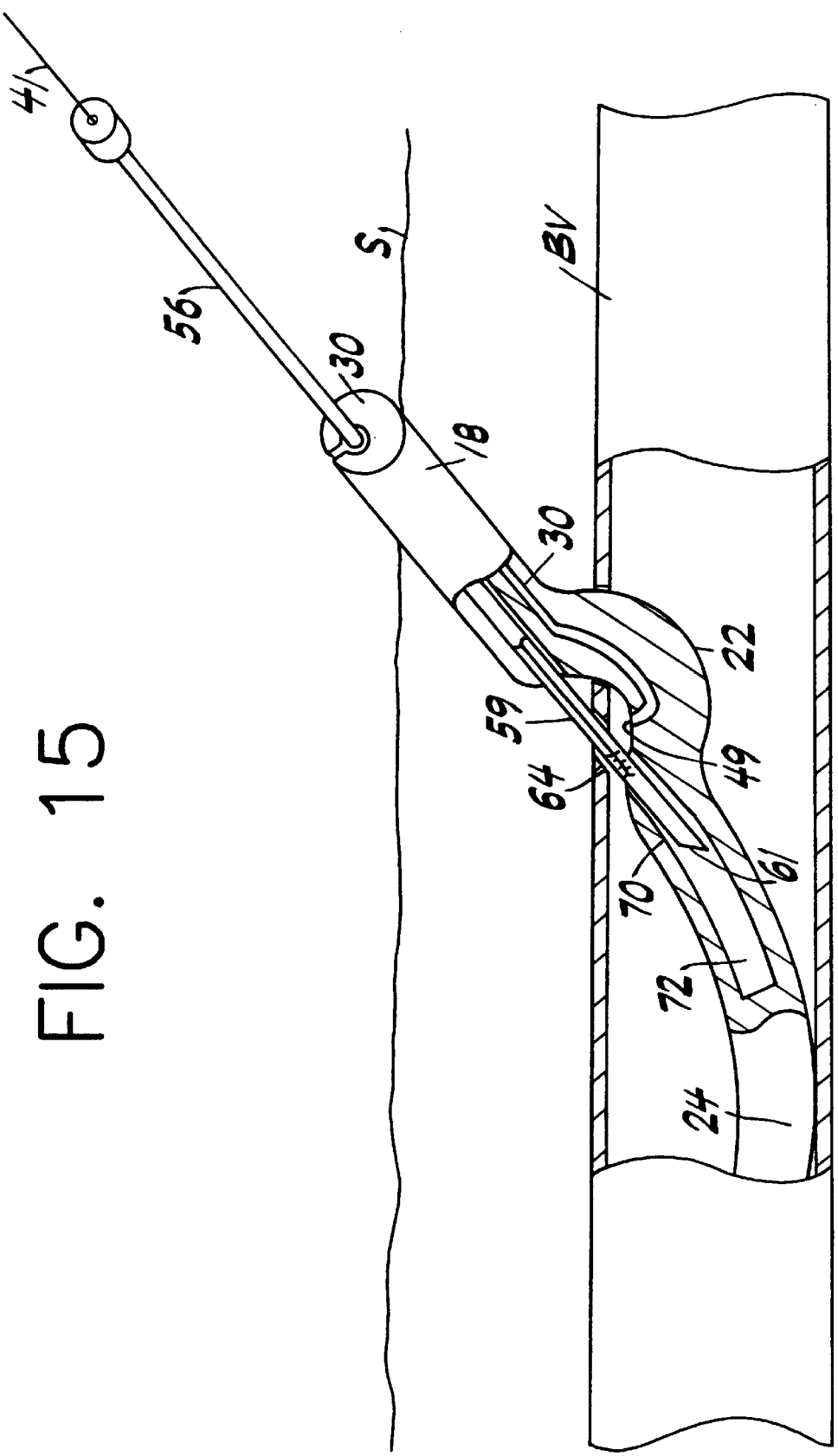
FIG. 15 shows a partially cross-sectional view of the blood vessel with a device according to the second embodiment of the present invention in a first desired position.
Figure 16:
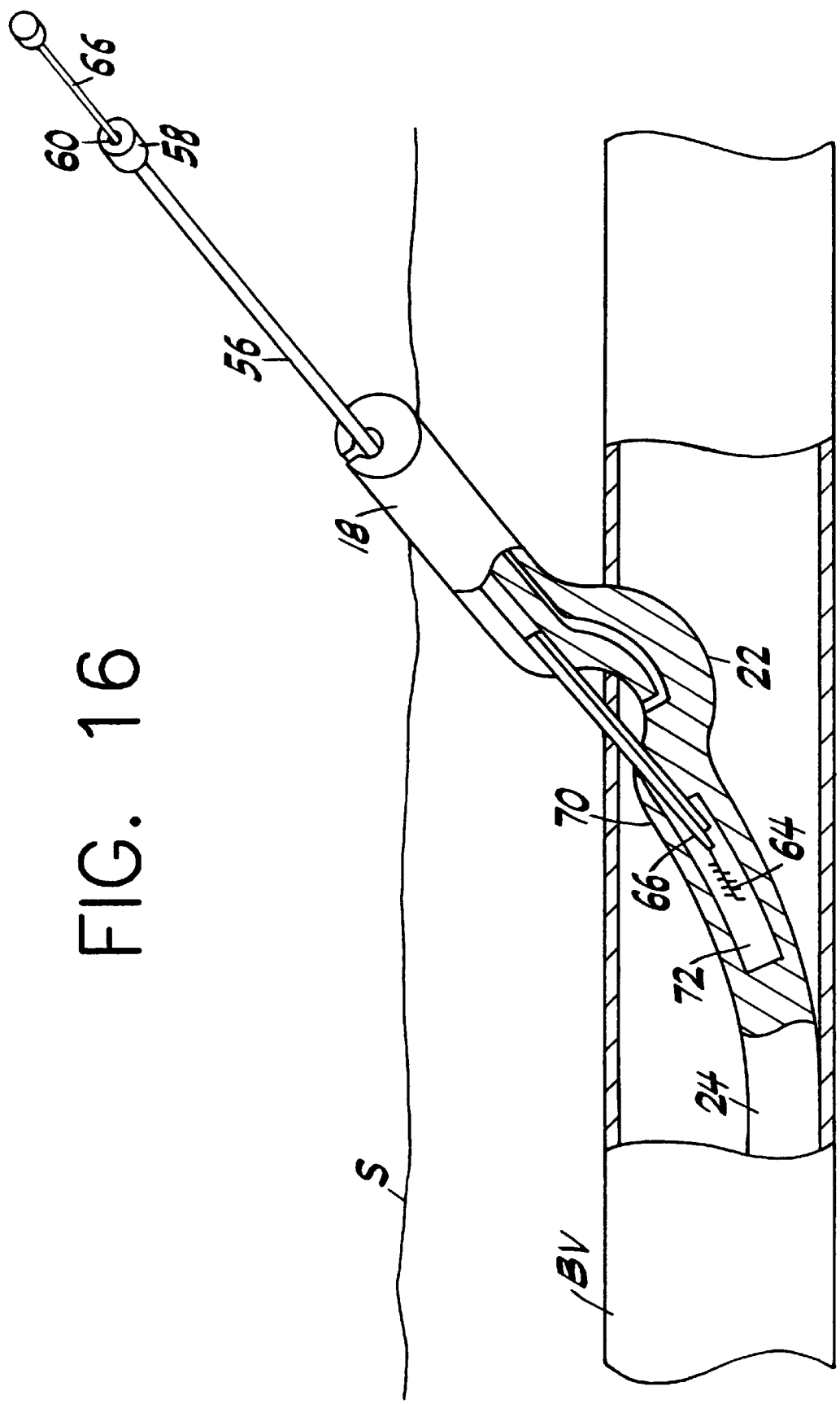
FIG. 16 shows a partially cross-sectional view of the blood vessel with a device according to the second embodiment of the present invention in the first desired position where a suture has been passed through the wall of the blood vessel and introduced into a suture retention chamber.

As shown in FIGS. 8–10, the doctor withdraws the device 1 from the body and detaches the suture 41 from the ends of the needles 37 and ties the two ends together in a slip knot which is urged inward toward the blood vessel and drawn tight in order to seal the puncture. Of course, those skilled in the art will appreciate that, once the two ends of the suture 41 have been drawn through the blood vessel wall, various other methods of fastening the two ends together may be employed.

FIGS. 11–19 show a suturing device according to a second embodiment of the present invention. The flexible tube 16 of the device 1' according to the second embodiment is preferably similar in size and flexibility to the device 1 of the first embodiment and differs only as described below. In addition, those skilled in the art will recognize that, except where specifically stated, each of the variations described above in reference to the first embodiment may also be applied to all other embodiments.

As seen in FIG. 12, the cross-section of the proximal part 18 of the device 1' shows a flash back lumen 30 of circular cross-section. The flash back lumen 30 of this embodiment extends from the first end 20, through the proximal part 18 to an opening 49 formed adjacent to the opening 68.

In addition, instead of the needle withdrawal lumen 26 of the first embodiment, the proximal part 18 of the device 1' includes a substantially circular puncture needle channel 50 extending from the first end 20 of the device 1' to an opening 52 at a proximal end of the central arcuate portion 22. This puncture needle channel 50 is also shown including an optional slot 54 extending through the surface of the flexible tube 16 along the length of the puncture needle channel 50.

A puncture needle 56, having an increased diameter gripping surface 58 at a proximal end, is slidably received in the puncture needle channel 50. The puncture needle 56 includes a central channel 59 extending from an opening 60 formed in the gripping surface 58 to an opening 61 formed in a distal end 62 of the puncture needle 50. One suture 41, integrally formed with or coupled to a respective anchor member 64, is received within the central channel 59. The anchor member 64 may be constructed as a coiled stainless steel spring.

Those skilled in the art will recognize that, if the puncture needle 56 is provided with a slot extending from a proximal end to a distal end thereof, a suture loop 41' may be formed with a single suture 41 having anchor members 64 at both ends. That is, after a first end of the suture has been inserted into the suture retention chamber 72, a first length of this suture 41 may be drawn out through the slot and a second anchor member 64 attached to a second end of the suture 41 may be inserted into the suture retention chamber 72 through a second portion of the blood vessel wall as described above. Thereafter, the device 1' is withdrawn from the body and the two ends of the suture loop 41' are tied together and, using known techniques, the knot is maneuvered so that it ends up on the outside of the blood vessel.

A plunger 66 is slidably received within the central channel 59 so that the anchor member 64 is located between the opening 61 and a distal end of the plunger 66 so that, when the plunger 66 is urged distally into the central channel 59, the anchor member 64 is moved toward the opening 61.

An opening 68 opposite the opening 52 at a distal end of the central arcuate portion 22, extends through a needle reception slot 70 to a suture retention chamber 72 which has an increased diameter relative to the needle reception slot 70. Those skilled in the art will recognize that many variations may be made to the structure of the anchor member 64 so long as sufficient stiffness is maintained and the anchor member is dimensioned so as to prevent the suture 41 from being withdrawn from the suture retention chamber 72 during withdrawal of the device 1' from the body.

In operation as shown in FIGS. 15–19, the device 1' is positioned with the central arcuate portion 22 straddling the blood vessel wall with the openings 52 and 68 on opposite sides of the wall (proximal and distal, respectively) and rotated to a desired position as described above in regard to the device 1 of the first embodiment.

As described above in regard to the device 1, the flash back lumen 30 may be used to determine whether or not the device 1' is in the desired position. Specifically, when the device 1' is in the desired position, blood should be observed only in the flash back lumen 30, not in the needle channel 50. Blood in the needle channel 50 indicates that the device 1' has been advanced too far into the blood vessel. That is, blood in the needle channel 50 indicates that the opening 52 is improperly positioned within the blood vessel. When the device 1' is properly positioned, the doctor presses upon the gripping surface 58 to urge the a sharp, distal end of the puncture needle 56 distally out of the opening 52, through the wall of the blood vessel and into the opening 56.

When the puncture needle 56 has been inserted into the suture retention chamber 72, the doctor pushes the plunger 66 distally within the central channel 59 to release the anchor member 64 into the suture retention chamber 72. The puncture needle 56 is then withdrawn from the suture retention chamber 72 and the plunger 66 is completely withdrawn from the central channel 59.

Where the device 1' includes the optional slot 54, the suture 41 may then be withdrawn from the puncture needle channel 50 through the slot 54. This allows the diameter of the puncture needle channel 50 to be minimized while providing sufficient room for the puncture needle 56 to pass therethrough. Then a second anchor member 64 and a second suture 41 are inserted into the central channel 59.

Figure 17:
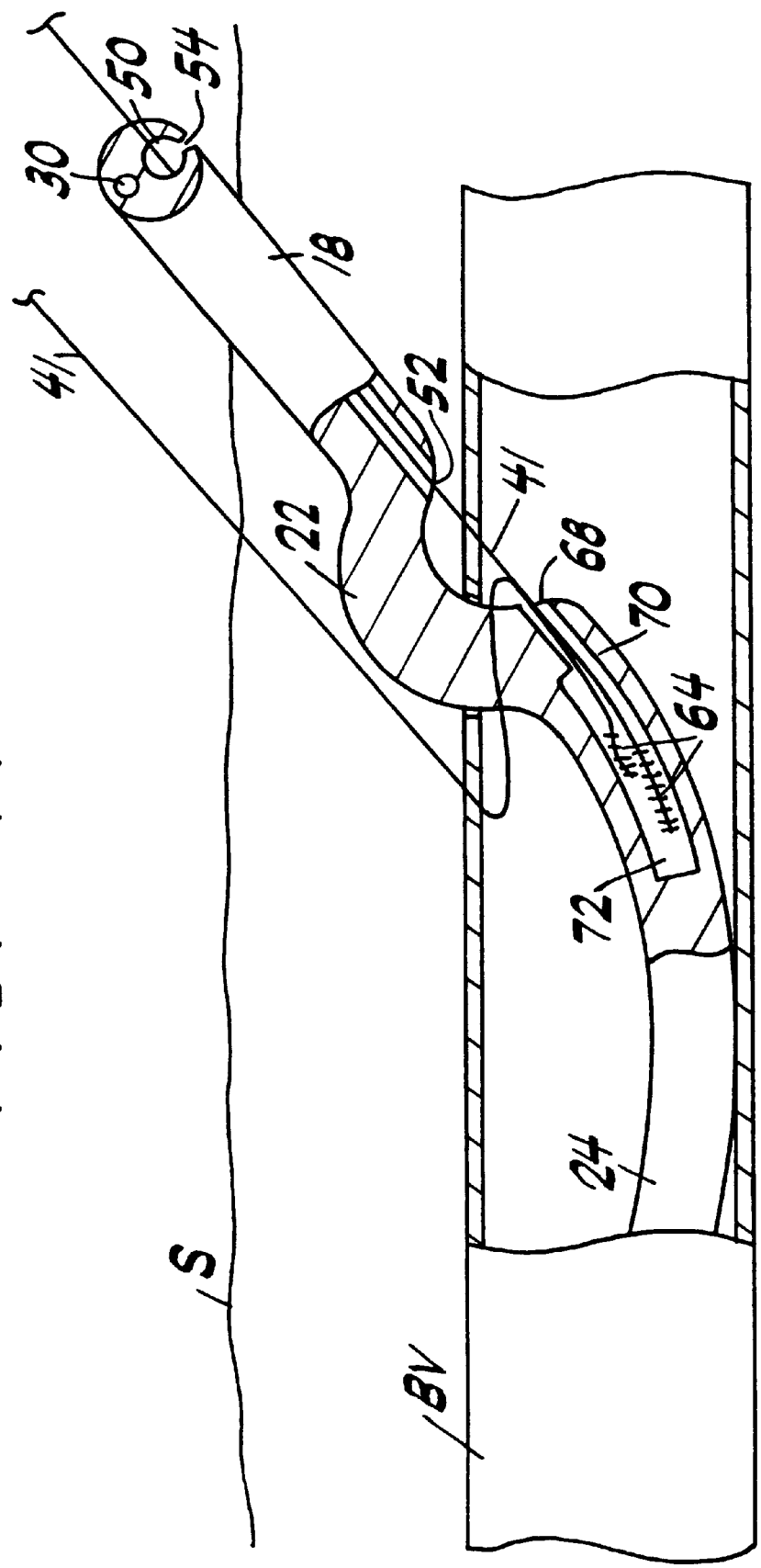
FIG. 17 shows a partially cross-sectional view of the blood vessel with a device according to the second embodiment of the present invention in a second desired position.
Figure 18:
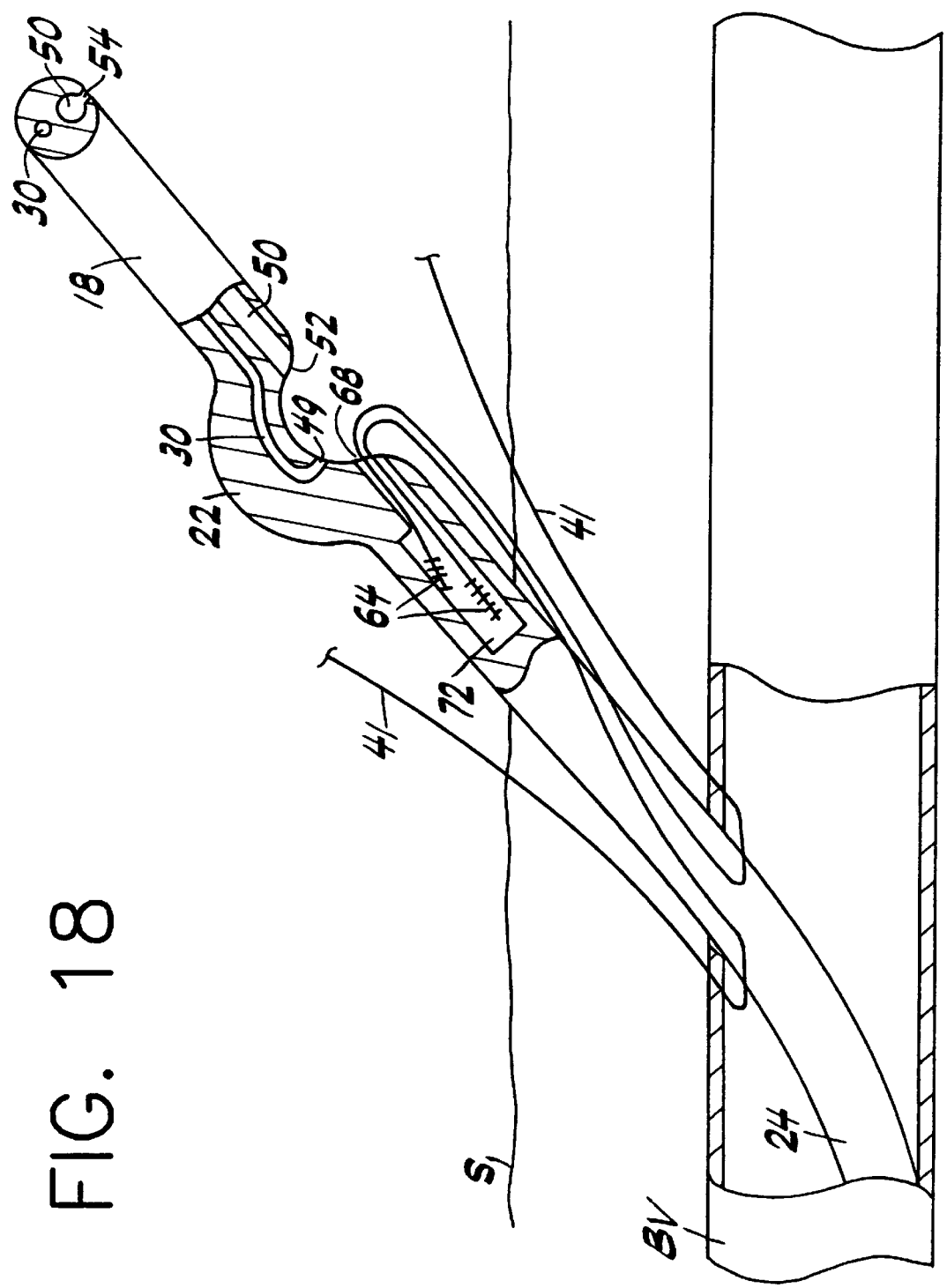
FIG. 18 shows a partially cross-sectional view of the blood vessel wherein the device according to the second embodiment has been partially withdrawn from the blood vessel.
Figure 19:
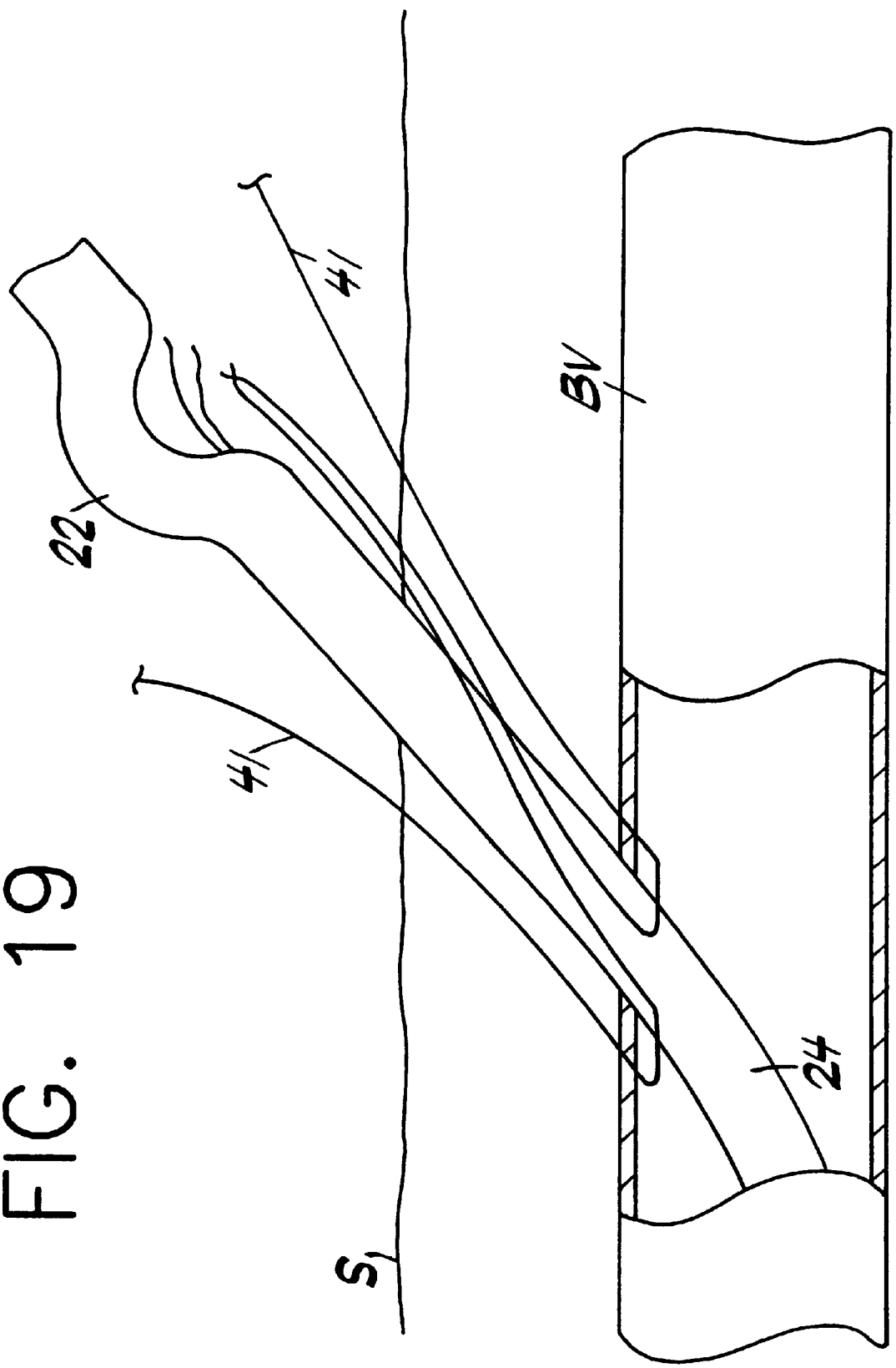
FIG. 19 shows a partially cross-sectional view of the blood vessel wherein the sutures have been severed from the anchor members and tied together.
Figure 20:
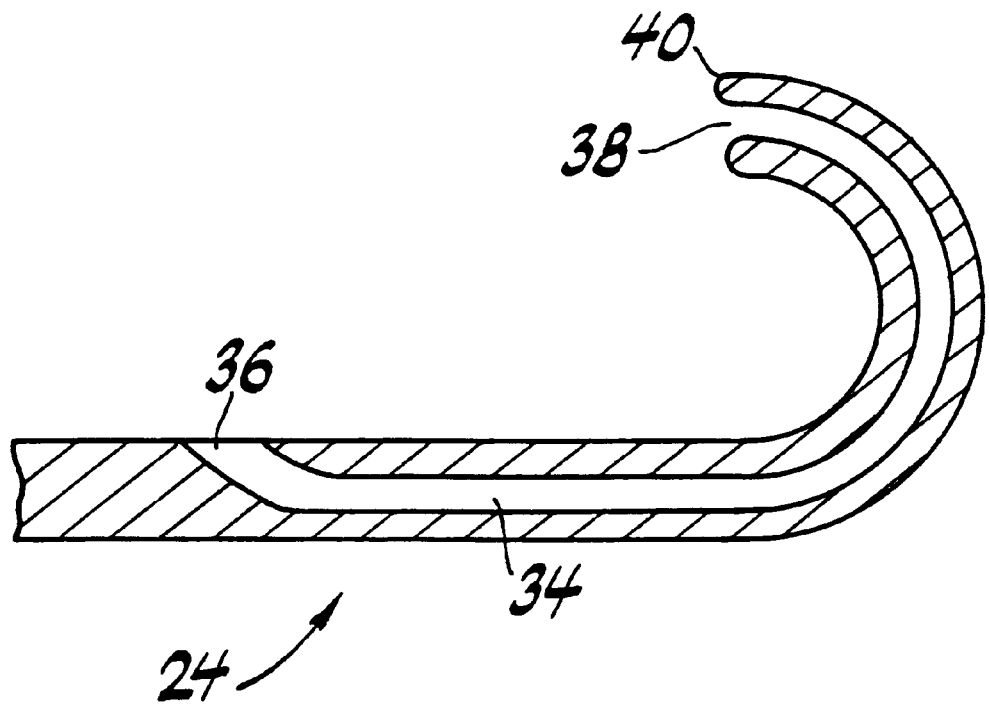
FIG. 20 shows a side view of a cross-section of a distal portion of a suturing device according to a third embodiment of the present invention.

As shown in FIG. 17, the doctor then reorients the device 1' into the second desired position, as described above in regard to the first embodiment, the doctor presses upon gripping the surface 58 to urge the sharp, distal end of the puncture needle 56 distally out of the opening 52, through the wall of the blood vessel and into the opening 56 so that the opening 61 is within the suture retention chamber 72. Thereafter, the doctor inserts the plunger 66 into the central channel 59 and pushes it forward to release the anchor member 64 and the second suture 41 into the suture retention chamber 72. Those skilled in the art will understand that, instead of inserting a second suture 41 at this point, a gripping device may be introduced through the central channel 59 into the suture retention chamber 72 to grab and retrieve the anchor member 64 and draw it out through the central channel 59. This allows for the formation of a suture loop 41' without the need to knot two separate strands of suture 41 together.

Figure 24:
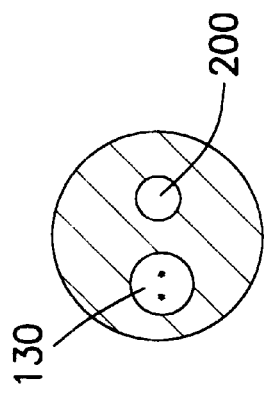
FIG. 24 shows a cross-sectional view of the suture device of FIG. 23 taken along the line 24—24.

The doctor then withdraws the device 1' from the body, as shown in FIG. 22, so that the ends of the sutures 41 extending from the opening 68 may be cut to release the sutures from the anchor members 64. Then, as shown in FIGS. 23 and 24, these ends of the sutures 41 are tied together and the other ends are knotted together and tightened to seal the puncture.

Those skilled in the art will understand that, for larger punctures, the device 1" may be used to insert as many sutures 41 as are required to seal the puncture. Specifically, in order to close punctures larger than size 9.0 French, a single suture 41 may not be sufficient. Therefore, instead of using the device 1" as described above to insert two sutures 41 approximately 180° apart, a doctor may, for example, insert four sutures 41 at 90° intervals using the technique described above. Then, when the device 1" has been withdrawn from the body, the doctor must knot together a first pair of sutures 41 which are separated by approximately 180° and then knot the second pair. The two pairs of sutures 41 may be distinguished by color coding or any similar technique.

A device 1" according to a third embodiment of the present invention is shown in FIGS. 25 and 26. Aside from a modified distal part 24 as described below, the construction and operation of the device 1" may be identical to either of the first and second embodiments.

Specifically, the distal part 24 of the device 1" is constructed so that it has enhanced flexibility relative to the proximal part 18. In addition, the distal part 24 is biased so that, when in an unstressed state, it is "J" shaped—that is, the distal part 24 is curved so that the distal opening 38 formed in the second end 40 faces proximally. This facilitates insertion of the device 1" so that it contacts an inner wall of the blood vessel without damaging it. Specifically, the flexibility and "J" shape of the second end 40 allows the second end 40 to deflect away from the blood vessel's lining without penetrating or damaging the lining thereof. Of course, when received on the guide wire 44, the "J" shape of the distal part 24 will be less pronounced. However, the bias will maintain a slight curvature of the second end 40 deflecting the impact of the device 1" from the inside lining of the blood vessel.

Figure 21:
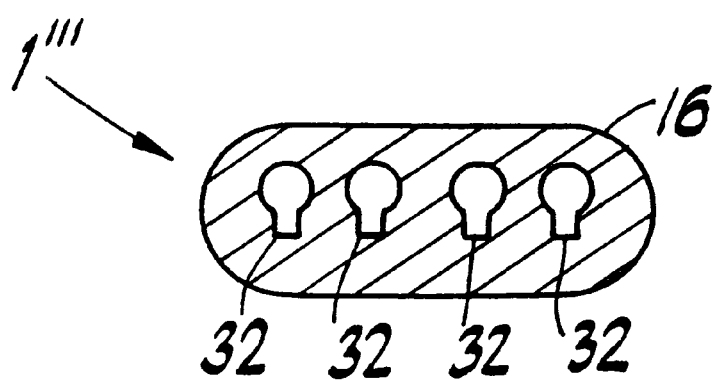
FIG. 21 shows a cross-section of a distal portion of a device according to the fourth embodiment of the invention.

As described above, in order to close punctures larger than size 9.0 French, a single suture 41 may not be sufficient. Thus, as shown in FIG. 21, a device 1''' according to a fourth embodiment of the invention may receive four needles 37 arranged side-by-side in four needle retention bores 32 formed in a flexible tube 16 of substantially oval cross-section. Other than the oval cross-section and the provision of four needles, the construction and operation of the device 1''' is similar to that of the device 1 according to the first embodiment.

The oval cross section increases the stiffness of the device 1''' in the plane in which the four needles lie side-by-side, while retaining flexibility to bend perpendicularly to that plane. The four needles 37 of the device 1''' are coupled together in pairs and each pair of needles will be positioned so that the needles 37 of each pair penetrate the wall of the blood vessel on opposite sides of the puncture (approximately 180° apart). When the device 1''' has been removed from the body, each pair is then knotted together and the two knots are tightened to seal the puncture.

Of course, those skilled in the art will understand that each of the variations of the device 1 according to the first embodiment may also be applied to the device 1'''. Similarly, those skilled in the art will recognize that four needles 37 may be received in a device 1''' having two needle retention bores 32, each being of a length sufficient to hold two needles 37 arranged in series end-to-end.

FIG. 22 shows a further embodiment of a suture device 101 according to the present invention. In this embodiment, the needles 137 are deployed simultaneously, eliminating the need to rotate the device 101 within the opening in the anatomical structure. This is achieved with a device 101 formed as an elongated member 116 having a rigid proximal portion 118 and a flexible distal portion 124 connected by a central portion 122. The proximal portion 118 and the distal portion 124 are both, for example, substantially circular in cross section. A distal end 121 of the proximal portion 118 has, for example, a slightly larger diameter than the rest of the proximal portion 118, forming a stop 221. The central portion 122 is, for example, oval or oblong in cross section. Moreover, unlike the central arcuate portion 22 of the other embodiments of the device (1, 1", etc.) of the present invention, the central portion 122 may be substantially straight.

As can be seen from FIG. 23, the proximal portion 116 has, for example, a pair of axially-running lumens extending therethrough: a position indication lumen 200 and a suture lumen 130. The position indication lumen 200 extends from a proximal position opening 201 in a proximal end 120 of the proximal portion 118 to a central position opening 202 in the central portion 122. In the central portion 122, the position indication lumen 200 turns, for example, 90° outward, so that the position indication lumen 200 runs radially outward until it terminates at the central position opening 202.

The suture lumen 130 extends from a proximal suture opening 131 in the proximal end 120 of the proximal portion 118 to a needle chamber 132 disposed in the distal portion 124. The suture lumen 130 is also connected to a central suture opening 203 in the central portion 122. The central suture opening 203 extends radially outward from the suture lumen 130. However, the central suture opening 203 runs, for example, in an opposite direction from the position indication lumen 200, so that the central suture opening 203 and the central position opening 202 are on radially opposite sides of the central portion 122.

As shown in FIG. 24, the suture lumen 130 is, for example, substantially oval or oblong in cross section while the position indication lumen 200 is, for example, substantially circular in cross section.

Further details of the elongated member 116 are shown in FIG. 25. The distal portion 124 includes, for example, a single, axially-running needle chamber 132 holding, for example, a pair of needles 137. The needles 137 are not fully contained in the needle chamber 132. Instead, part of each needle 137 extends through a needle channel 123.

Each needle channel 123 runs substantially axially from the needle chamber 132 to a needle channel opening 133. However, as can be seen from FIG. 25, each needle channel 123 also runs, for example, slightly radially outwardly as it extends from the needle chamber 132 to the respective needle channel opening 133. The needle channel openings 133 appear on a proximal face 233 of the distal portion 124, and are located, for example, on radially opposite sides of the proximal face 233 of the distal portion 124. Thus as the needles 137 exit the needle channels 123, the needles 137 move substantially in the proximal direction (towards the right as seen in FIG. 25), but also slightly outwardly in opposite radial directions from one another.

In addition to being radially opposite from each other, the needle channel openings 133 are each, for example, radially offset 90° from the central position opening 202 and the central suture opening 203. The needle channel openings 133 are, for example, radially aligned with the minor axis of the oval central portion 122, while the central position opening 202 and the central suture opening 203 are located, for example, on the major axis of the central portion 122.

For example, two segments of a length of suture 141 are contained within the elongated member 116. The length of suture 141 is doubled over itself so that a suture loop 142 extends outside the proximal suture opening 131. Two segments of the length of suture 141 enter the suture lumen 130 via the suture opening 131 and exit the suture lumen 130 via the central suture opening 203. Each of the two segments then enters a respective needle channel 123 and travels ultimately to the needle chamber 132. The end of each segment of the length of suture 141 is connected to the distal end of a respective one of the needles 137 within the needle chamber 132.

As can also be seen from FIG. 25, the device 101 according to this embodiment may be manufactured in three sections: a first section including the proximal portion 118, the central portion 122, and the proximal end of the distal portion 124 containing the needle channels 123; a second section including only that part of the distal portion 124 containing the needle chamber 132; and a third section including only a soft tip 140 at the distal end of the distal portion 124. These various sections may preferably be formed separately, for example by extrusion or molding, and then fixed together.

FIGS. 26, 27 and 28 show cross-sectional views of the device 101 taken along lines 26—26, 27—27, and 28—28 of FIG. 25, respectively. FIG. 26 shows the distal portion 124 with the needle chamber 132 therein. The needle chamber 132 contains, for example, two needles 137, each needle 137 connected to an end of a length of suture 141. FIG. 27 shows the central portion 122 and the proximal face 233 of the distal portion 124. The suture 141 passes from the suture lumen 130 and central suture opening 202 into the needle channel openings 133. FIG. 28 shows the proximal portion 118 with the position indication lumen 201 and the suture lumen 130 therein. The suture lumen 130 contains two segments of a length of suture 141.

Figure 30:
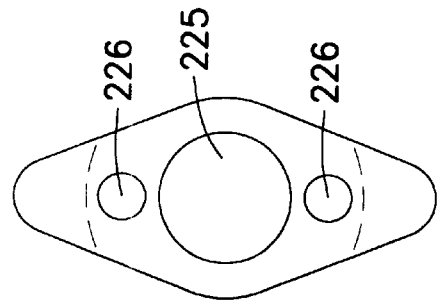
FIG. 30 shows a cross-sectional view of the needle receiving body of FIG. 29 taken along line 30—30.
Figure 29:
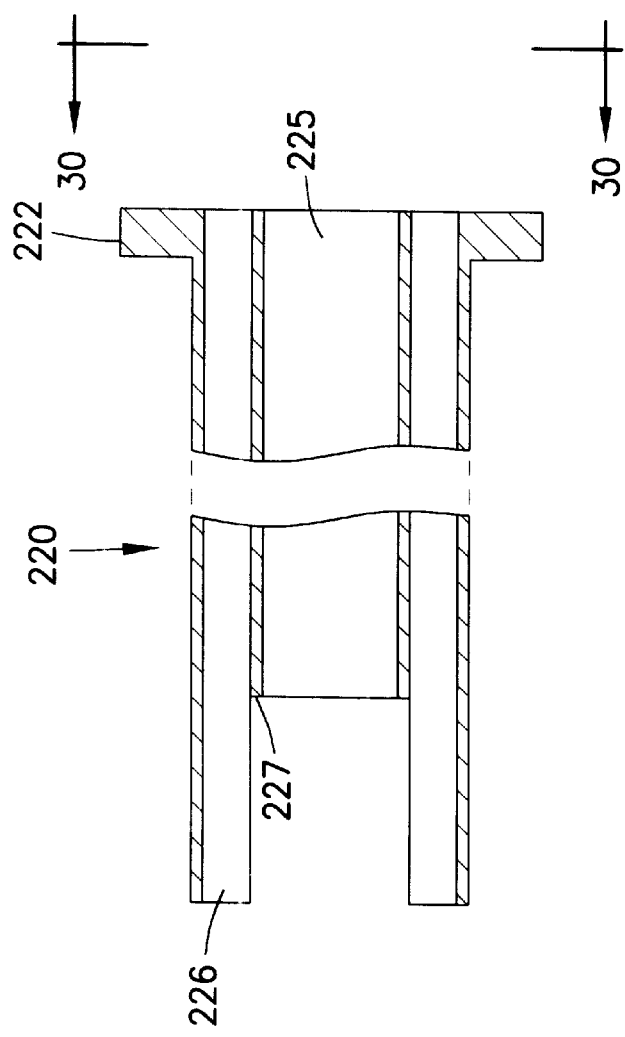
FIG. 29 shows a side view of a needle receiving body according to the present invention.

A needle receiving body 220 of the device 101 is shown, for example, in FIGS. 29 and 30. The needle receiving body 220 as shown is an elongated member having a generally annular cross section for most of its length. Two protrusions 222 extend, for example, radially outward from a proximal end 221 of the needle receiving body 220. The protrusions 222 assist in handling the needle receiving body 220.

The needle receiving body 220 has a device lumen 225 extending axially therethrough. The device lumen 225 shares, for example, the same axis as the needle receiving body 220 as a whole (i.e. the device lumen 225 is radially centered within the needle receiving body 220). The device lumen 225 has a first inner diameter substantially the same diameter as, or slightly larger than, the outer diameter of the proximal portion 118 and a second inner diameter slightly larger than the first inner diameter so that an abutment 227 is formed at the intersection of the portion having the first inner diameter and the portion having the second inner diameter.

On opposite side of the device lumen 225 extend, for example, a pair of axially-running needle receiving channels 226.

The inner diameter of the needle receiving body 220 allows in to be slidably placed upon the elongated member 116. The needle receiving body 220 travels down the proximal portion 118, and slides distally until the abutment 227 of the needle receiving body 220 contacts the stop 221 on the elongated member 116. At this point the needle receiving body 220 may be fixedly or rotatably joined to the elongated member (for example, as part of the manufacturing process), or may remain slidably and/or frictionally coupled with the elongated member 116. The latter allows the use of a device 101 without a needle receiving body if so desired, for example when closing skin wounds or during certain laparoscopic procedures.

Figure 31:
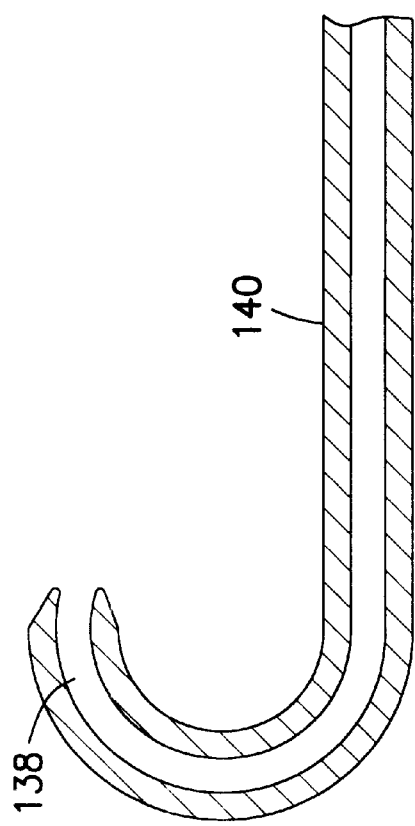
FIG. 31 shows a side view of a distal end of another embodiment of the suture device according to the present invention.

FIG. 31 shows the tip 140 which is disposed at the distal end of distal portion 124. As seen from the Figure, the tip 140 may be a J-shaped, elongated member. The tip 140 may also, however, be formed as a straight member or any other shape, as dictated by the shape of the anatomical structure and surrounding tissues. The tip 140 includes, for example, an axially-running guide wire lumen 138 extending therethrough. The tip 140 may be formed of, for example, a soft or flexible material. The shape of the tip 140 and its material allow the tip 140 to be easily inserted into the anatomical structure.

Figure 32:
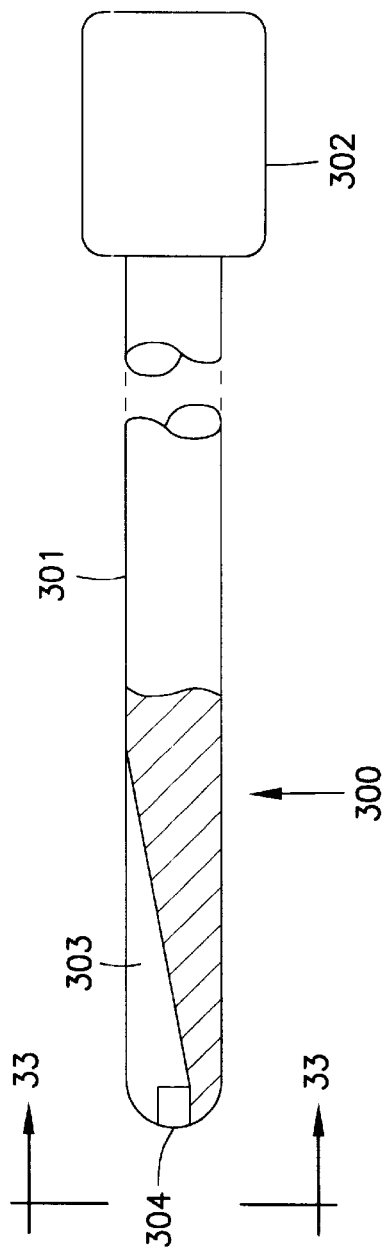
FIG. 32 shows a side view of a knot pusher according to the present invention.
Figure 33:
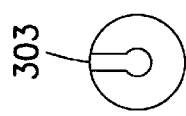
FIG. 33 shows a cross-sectional view of the knot pusher of FIG. 32 taken along line 33—33.
Figure 34:
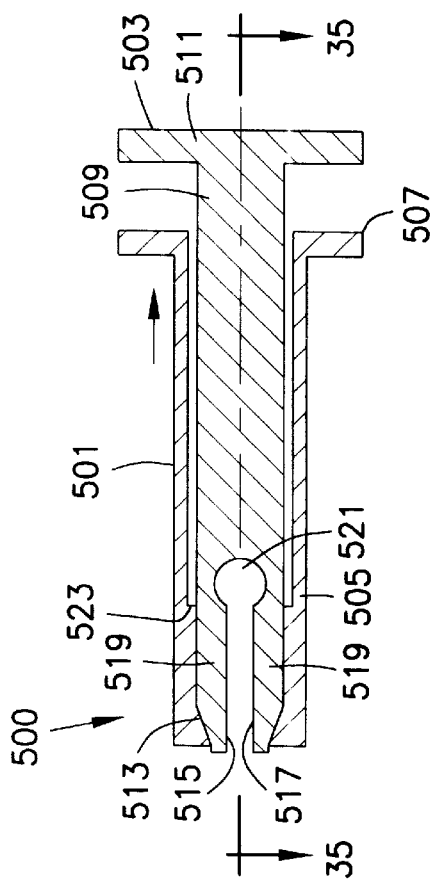
FIG. 34 shows a cross-sectional view of a suture crimping device according to the present invention.
Figure 35:
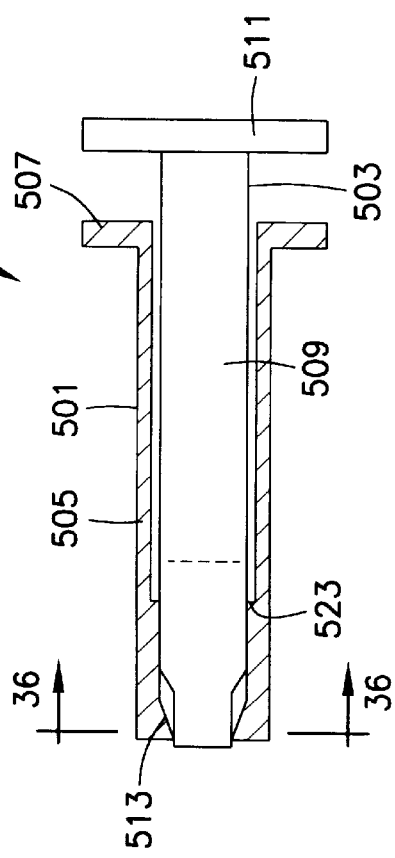
FIG. 35 shows a cross-sectional view of the suture crimping device of FIG. 34 taken along line 35—35 of FIG. 34.
Figure 36:
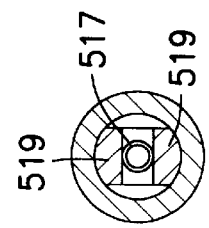
FIG. 36 shows a cross-sectional view of the suture crimping device of FIG. 34 taken along line 36—36 of FIG. 35.
Figure 38:
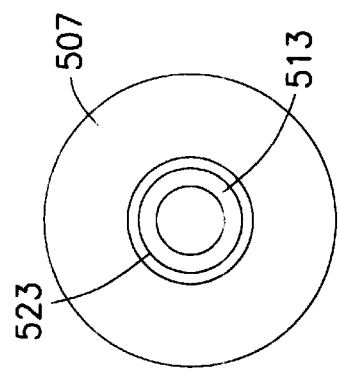
FIG. 38 shows a back view of the barrel of FIG. 37 taken along line 38—38 of FIG. 37.
Figure 37:
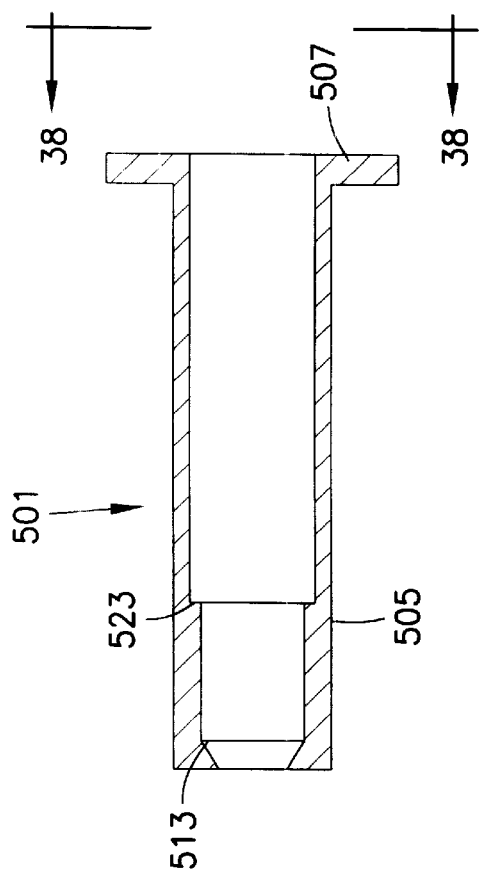
FIG. 37 shows a cross-sectional view of a barrel according to the present invention.

The device 101 according to this embodiment of the present invention may also include a knot pusher 300, as shown in FIGS. 32 and 33. The knot pusher 300 includes a longitudinal member 301 having, for example, a circular cross section. A knob 302 is disposed at a proximal end of the longitudinal member 301. The distal end of the longitudinal member 301 is, for example, rounded.

The distal end of the longitudinal member has an axially-extending slit 303 formed therein. The slit 303 has, for example, a constant width appropriately sized to accommodate two or more segments of a length of suture 141, but small enough so that a knot cannot enter the slit 303. The depth of the slit 303, however, decreases as the slit extends proximally from the distal end of the longitudinal member 301. The slit 303 has an initial depth, for example, slightly greater than the radius of the longitudinal member 301, and the depth decreases to zero, for example linearly, as the slit extends proximally.

The distal end of the longitudinal member 301 also has, for example, a circular recess 304 formed therein. The recess 304 intersects the slit 303, forming a continuous path through the elongated member 301. The recess 304 preferably has a radius greater than the width of the slit 303, and should generally be sized to accommodate a knot in the length of suture 141. Thus a knot in a length of suture 141 may be inserted into the recess 304 and the ends of the length of suture 141 pulled through the slit 303 to tighten the knot.

FIGS. 34 to 44 illustrate a second exemplary device and method for stabilizing the suture 141. These Figures show a suture crimping device 500, which clamps the free ends of suture 141 with a grommet 517. Generally, crimping device 500 includes a barrel 501 and a piston 503. Barrel 501 includes a shaft 505, preferably cylindrical in shape, and may also include a barrel hub 507 if desired. Similarly, piston 503 includes a preferably cylindrical shaft 509 and may include a piston hub 511. Piston 503 and barrel 501 are sized so that piston 503 may be inserted into barrel 501.

The distal ends of barrel 501 and piston 503 are constructed so that the distal end of piston 503 is compressed as it is inserted into barrel 501. In particular, barrel 501 includes an inner camming surface 513, and piston 503 includes an outer camming surface 515. The distal end of piston 503 is also constructed to receive a grommet 517. Grommet 517 is crimped as piston 503 is compressed, thereby clamping a suture 141 which may be threaded through the grommet 517.

The distal end of piston 503 preferably includes a pair of arms 519, which are flexible and easily compressible as piston 503 is advanced into barrel 501. To increase flexibility further, piston 503 may also include a relief hole 521 formed at the base of arms 519. To hold grommet 517, arms 519 are preferably provided with a recess 516, best illustrated in FIG. 39, although any retention mechanism may be utilized for this purpose. In addition, as illustrated in FIGS. 39 and 40, arms 519 are preferably laterally compressed near ends 520 to allow full advancement of piston 503 into barrel 501.

Grommet 517 is preferably circular, for example toroid, in shape, and may be formed of any suitable materials, for example metal, plastic, or biological material. Grommet 517 is preferably at least partially reabsorbable, but permanent materials may be used if desired. In a particularly advantageous construction, grommet 517 includes a plurality of layers. For example, grommet 517 may include an inner layer of adhesive such as cyonacrylate or fibrin, surrounded by an outer layer of permanent or resorbable material. Alternatively, grommet 517 may include an inner layer of permanent or resorbable material surrounded by an outer layer of, for example, collagen or adhesive.

Figure 42:
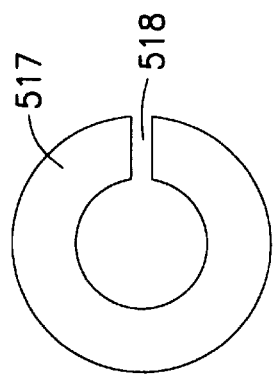
FIG. 42 shows an exemplary grommet according to the present invention.
Figure 43:
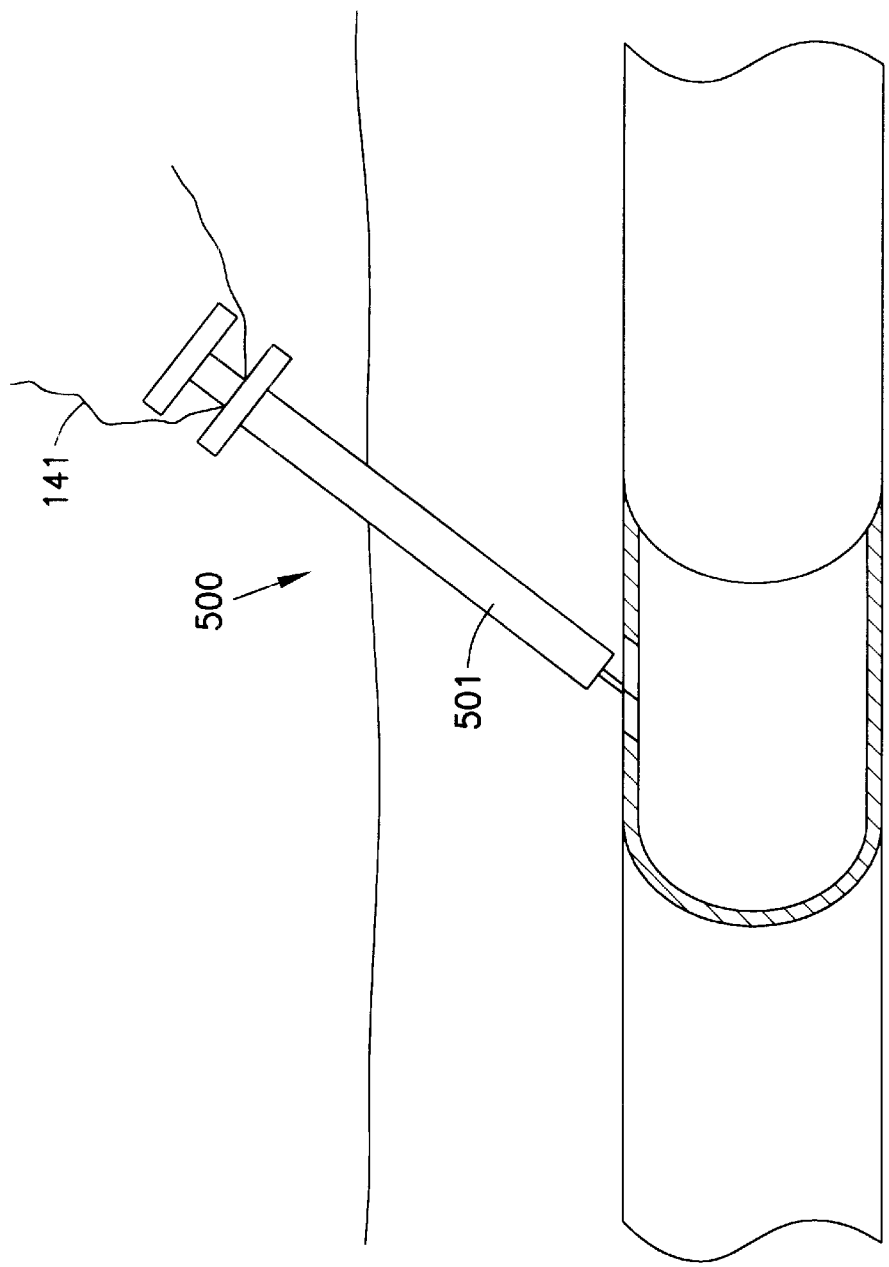
FIG. 43 shows a side view of the suture crimping device of FIG. 34 with a suture drawn therethrough.
Figure 44:
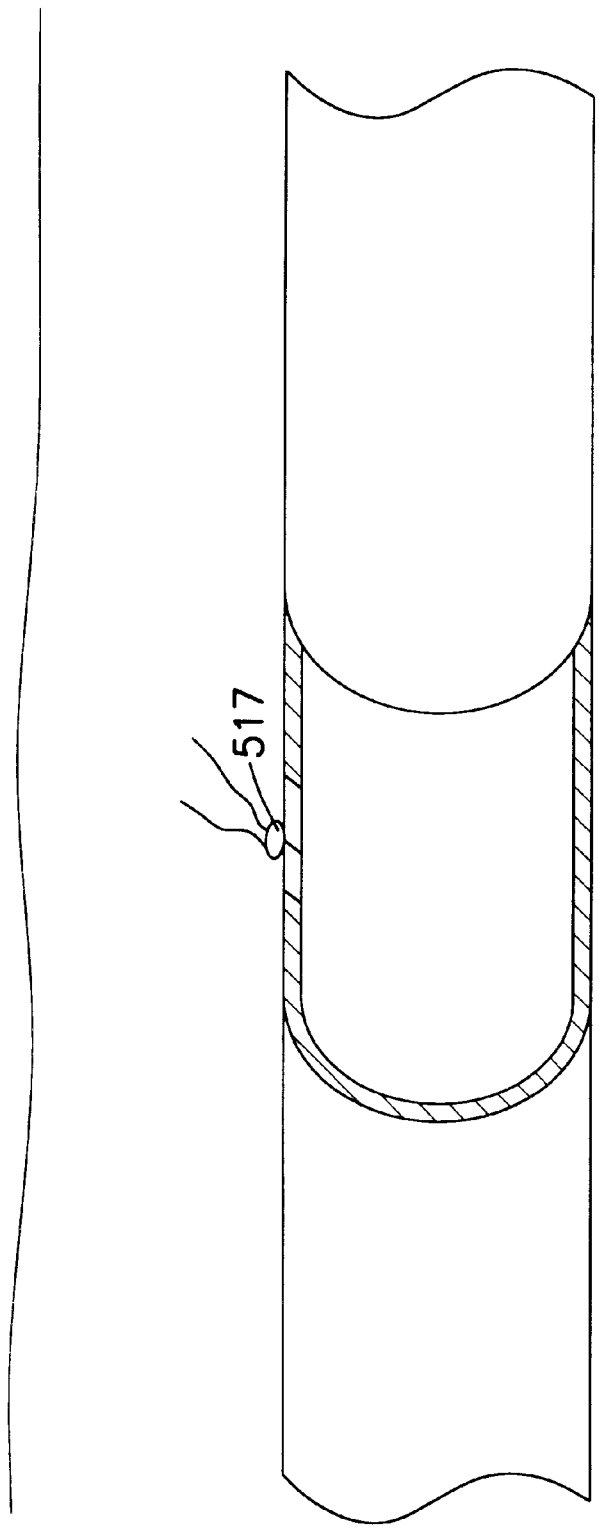
FIG. 44 shows an exemplary grommet according to the present invention clamping a suture.

As illustrated in FIGS. 43 and 44, a suture 141 may be threaded through barrel 501 so that the distal end of barrel 501 is oriented towards the blood vessel. Suture 141 may then be threaded through grommet 517. For this purpose, grommet 517 may include a transverse slit 518, as shown in FIG. 42. While tightening tension is applied to suture 141, piston 503 may be inserted into barrel 501 until camming surfaces 513 and 515 compress arms 519. This compression crimps grommet 517, clamping grommet 517 over suture 141. In this manner, suture 141 is quickly stabilized, sealing the puncture, without the need for tying a knot.

Barrel 501 preferably includes a stop 523. Stop 523 is formed at the abutment of two sections of barrel 501 having different interior diameters. Specifically, the distal end of barrel 501 may have a diameter slightly smaller than the diameter of a proximal section of barrel 501. The diameter of the distal end of the barrel 501 is preferably chosen to closely correspond to an outer diameter of the piston 503. Thus, as piston 503 is advanced into barrel 501, portions of the suture 141 received between the outer diameter of the piston 503 and the inner surface of the barrel 501 will be severed as relief hole 521 advances beyond stop 523. In this manner, the long ends of suture 141 are automatically removed from the crimped section of suture 141.

Figure 44A:
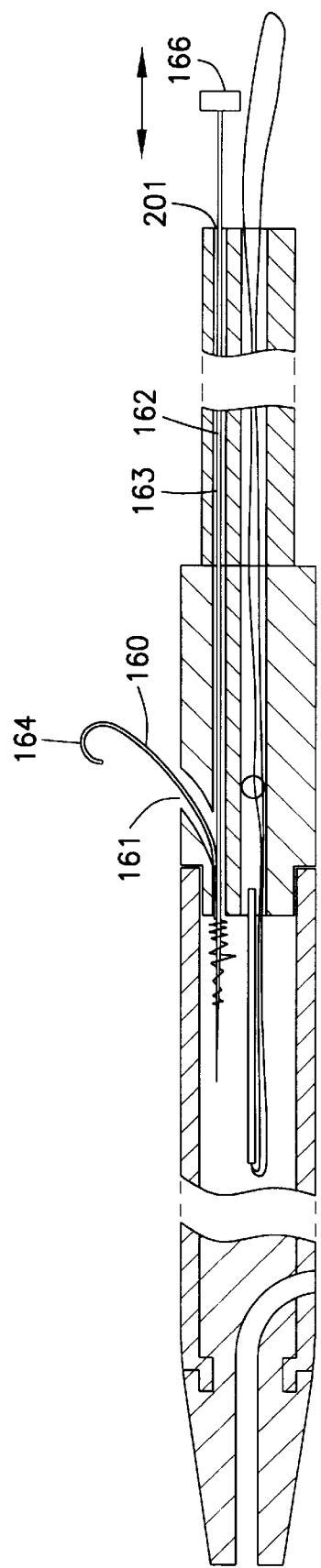
FIG. 44A shows an further exemplary embodiment of a suture device according to the present invention.
Figure 45:
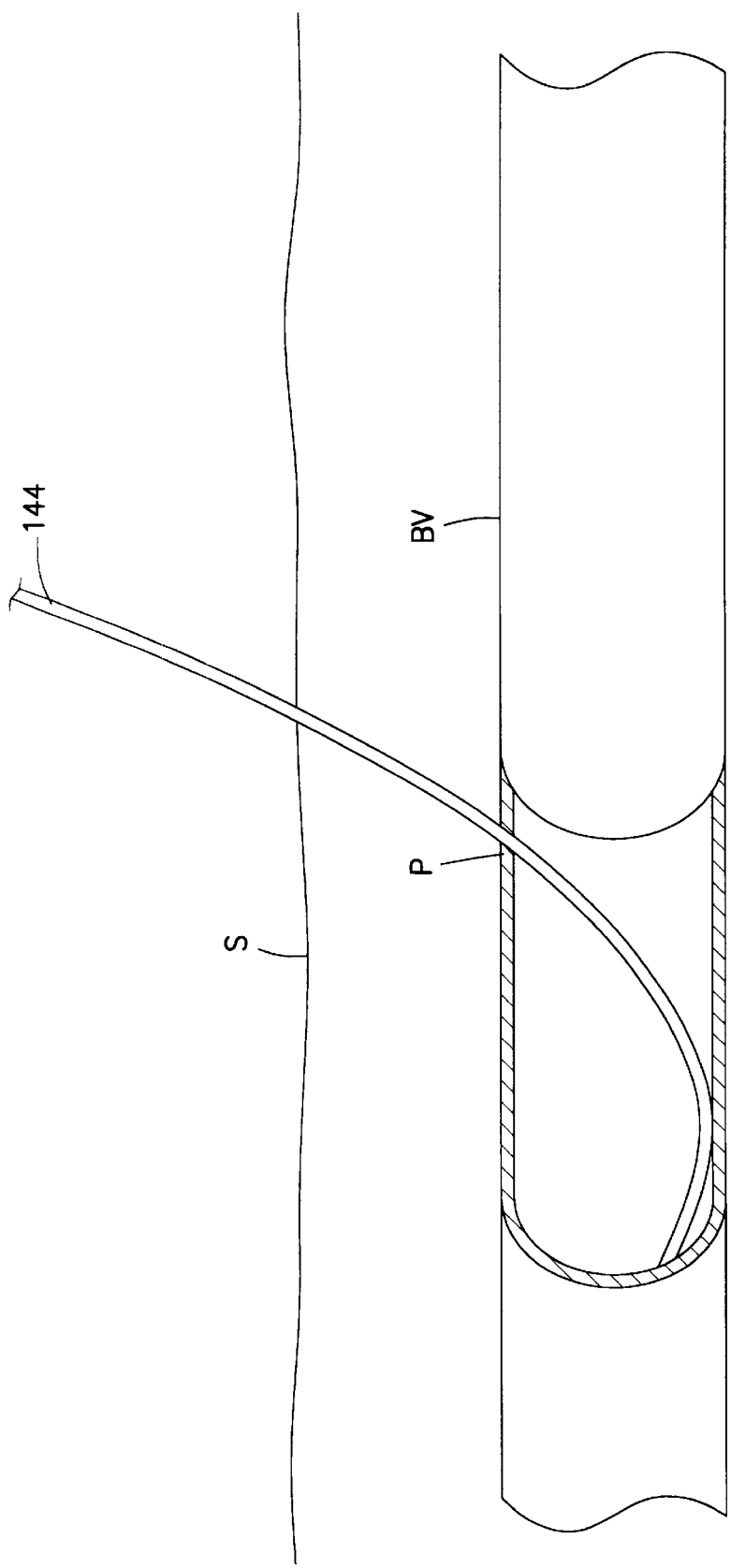
FIG. 45 shows a perspective view of a guide wire inserted into an anatomical structure, specifically a blood vessel.
Figure 46:
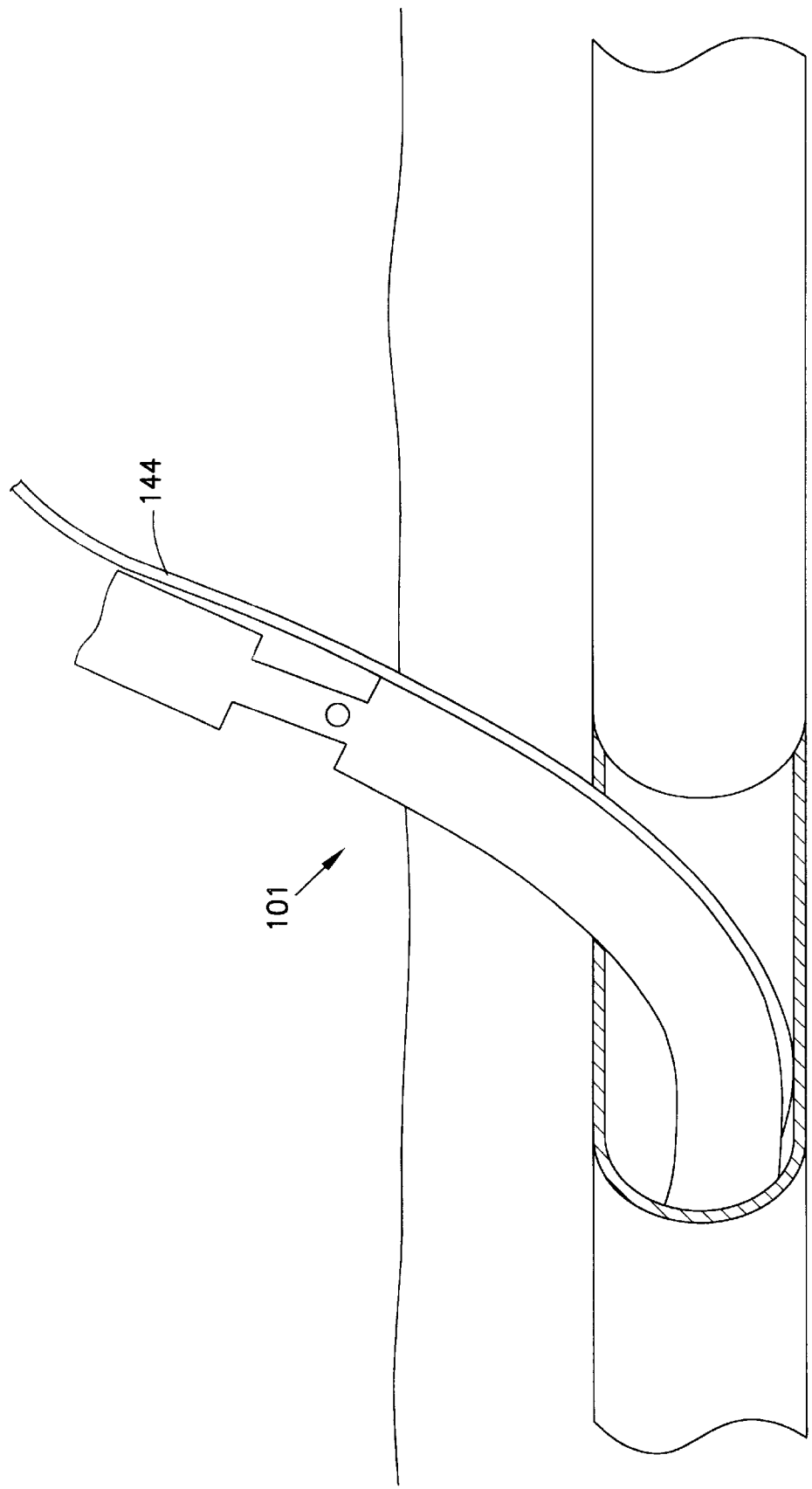
FIG. 46 shows a perspective view of a suture device according to the present invention partially inserted into an anatomical structure.
Figure 47:
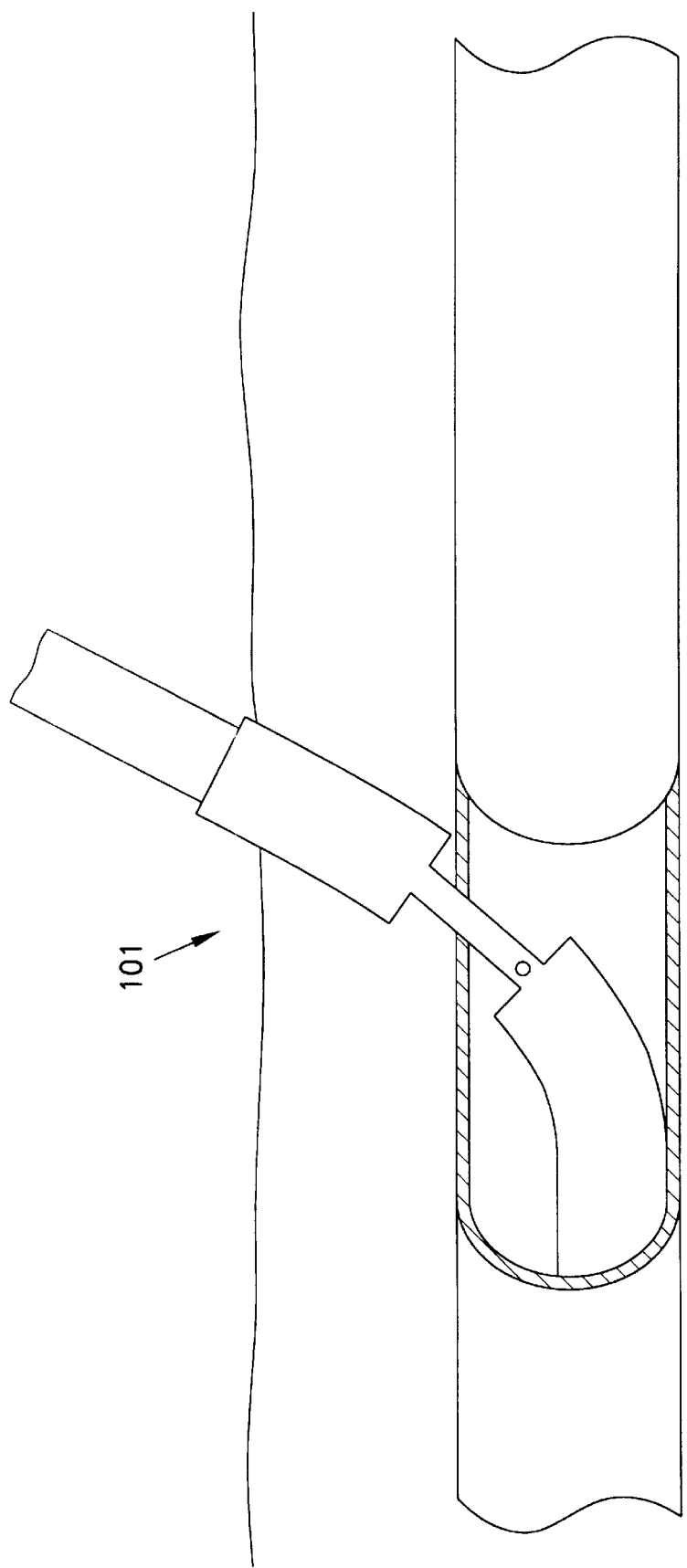
FIG. 47 shows a perspective view of the suture device of FIG. 46 inserted to a desired position in an anatomical structure.
Figure 48:
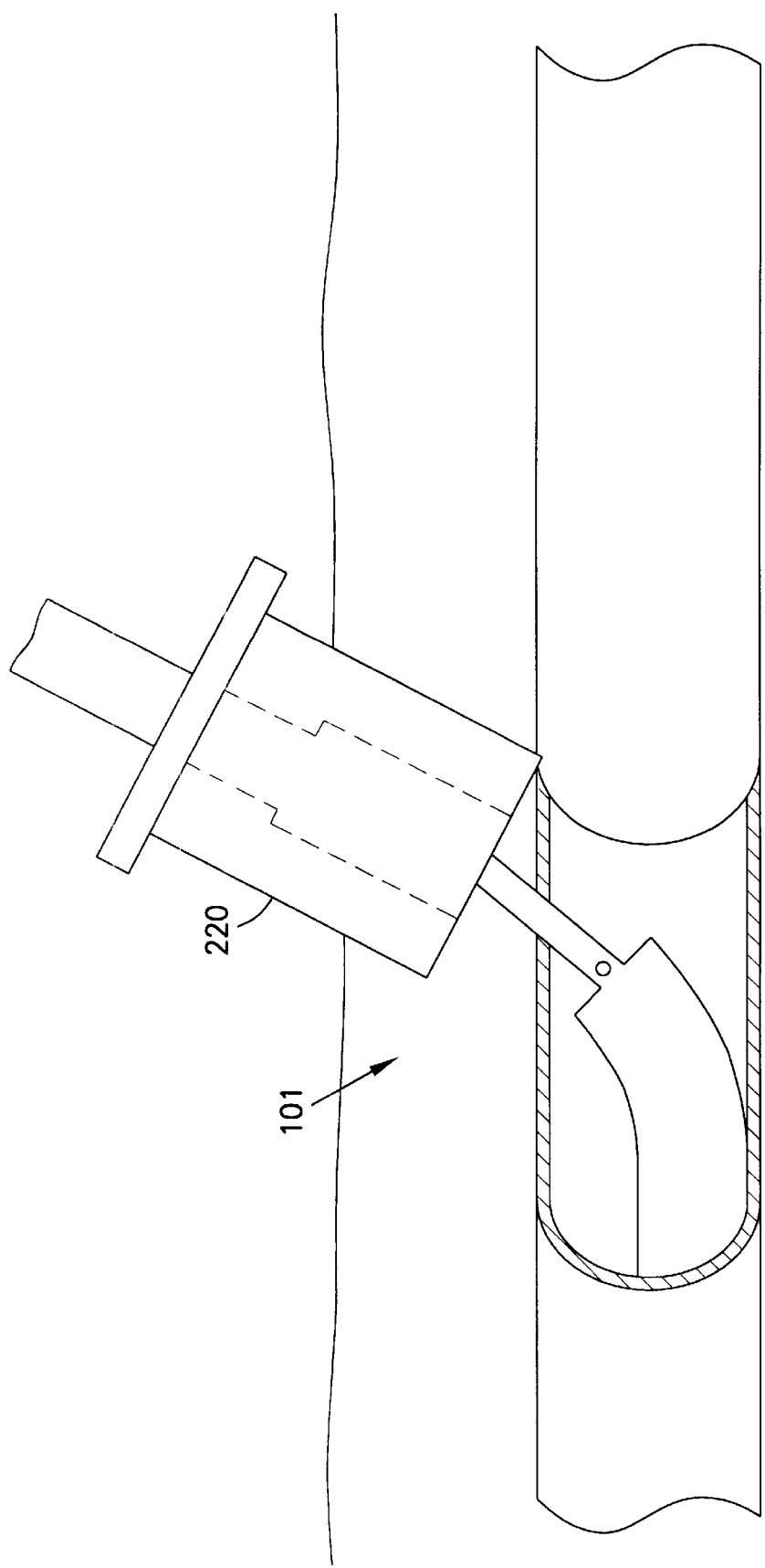
FIG. 48 shows a perspective view of the suture device of FIG. 26 with a needle receiving body according to the present invention.
Figure 49:
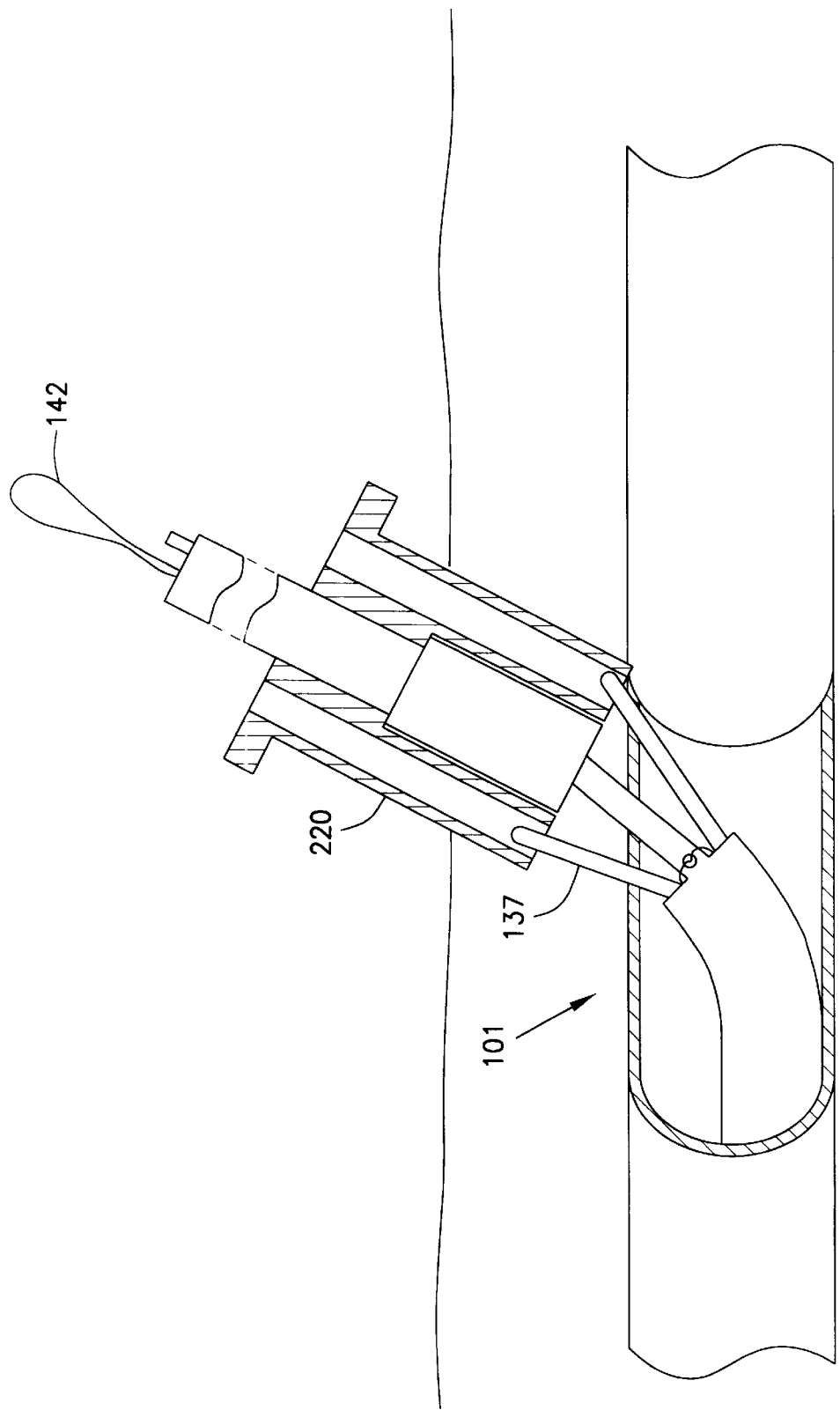
FIG. 49 shows a perspective view of the suture device of FIG. 48 with a pair of puncture needles partially deployed.

FIG. 44A illustrates a further exemplary embodiment of the present invention. In this embodiment, the control arm lumen 163 is shaped, for example, to house a retractable anchor 160 and an anchor control arm 162. In particular, the portion of the control arm lumen 163 extending radially outward may, for example, be slanted backward (i.e. proximally) toward the control arm opening 161.

Control arm 162 extends, for example, through the axial portion of control arm lumen 163, as shown in FIG. 44A, exiting the proximal position opening 201. Anchor 160 may be attached to the control arm 162 near a distal end of the control arm 162. Anchor 160 may be at least partially retained, for example, in the backward-slanting section of control arm lumen 163.

In an exemplary embodiment, anchor 160 is a flexible member. In an unbiased configuration, the end of the anchor 160 may form a curved anchor hook 164. This unbiased configuration may be obtained, for example, when the anchor hook 164 is outside the position indication lumen control arm lumen 163 as shown in FIG. 44A. When the anchor hook 164 is within the control arm lumen 163, the interior wall of the position indication lumen biases the anchor hook 164 to a substantially straight configuration.

It will be understood by one of skill in the art that the control arm 162, and the anchor 160 are capable of movement between retraced and extended positions. In the retracted position, the control arm 162 projects distally into the control arm lumen 163 so that anchor 160, including anchor hook 164, are retracted into the control arm lumen 163. Several features may be employed to limit the distal movement of the control arm 162, if desired. For example, a control arm stop 166 may be attached to the portion of control arm outside the suture device 101. The control arm stop 166 will contact the distal end of the suture device 101 when the control arm 160 reaches a distal-most position. Similarly, the distal end of control arm 162 may contact a distal end face of the control arm lumen 163, preventing further distal movement of the control arm 162. Alternatively, the diameter of the control arm 162 may increase moving away from the distal end, so that the wider-diameter section of the control arm 162 is prevented from entering a distal portion of the control arm lumen 163 having a smaller diameter. Other configurations are possible, and any suitable arrangement may be employed if desired.

When the control arm 162 is drawn to the extended position, the anchor 160 extends outside the control arm opening 161, and the anchor hook returns to a curved, unbiased configuration.

In practice, the anchor 160 may work in conjunction with, or as an alternative to, a position indication lumen 200 as described above. The suture device 101 may be inserted into the body with the control arm 162 and anchor 160 in, for example, the retracted position. As the device 101 approaches the desired position, the control arm 162 and anchor 160 may be moved to the extended position, so that the anchor hook 164 contacts the inside of the blood vessel and retains the suture device 101 in the desired position. Once the blood vessel has been suture as described above, the anchor 160 may be retracted and the suture device 101 removed from the body.

The operation of the device 101 according to this embodiment is shown in FIGS. 45–52. When an invasive procedure is performed on a patient which requires the insertion of a catheter into a blood vessel (or other structure within the body), an introducer sheath is inserted through the skin (S) into the patient's body through a puncture (P) in a wall of the blood vessel (BV). A guide wire 144 is inserted through the puncture to a target area within the blood vessel and a catheter is inserted through the introducer sheath, along the guide wire 144, to a target area within the blood vessel.

After the procedure is complete, the catheter and the introducer sheath are withdrawn and the guide wire 144 is left in place. A proximal end of the guide wire 144 is then inserted through the guide wire lumen 138 and the device 101 is inserted into the body and moved along the guide wire 144 through the puncture until the central portion 122 is located within the puncture (i.e. the walls of the blood vessel on opposite sides of the puncture surround the central portion 122). The major axis of the central portion 122 should be aligned with the length of the puncture so that the wall around the puncture is stretched as little as possible.

By observing the position indication lumen 201, the doctor may determine when the device 101 is in the desired position. Specifically, when the device 101 is inserted far enough into the blood vessel, blood will begin to be observed in the position identification lumen. Alternatively, an anchor 160, if provided, may also be used to position device 101.

As the device 101 is inserted into the blood vessel, the flexible tip 140 bends so that the device 101 is received within, and extends in the direction of the blood vessel without straining the vessel. In this position, the needle channels 123 are inside the blood vessel with the pointed tissue piercing ends of the needles facing proximally, that is, toward the proximal portion 118.

If desired, the needle receiving body 220 may then be introduced around the proximal portion 118 and slid down the proximal portion 118 until it reaches the stop 221. The needle receiving body may also be rotated, if necessary, to align the needle receiving lumens 226 with the needle channel openings 133 (assuming that the needle receiving body 220 is not fixedly attached to the elongated member 116).

With all the components of the device 101 in place, the operator may pull on the loop 142 in the length of suture 141. As the suture is withdrawn through the elongated member 116, it pulls the needles 137 out of the needle chamber 132 and the needle channels 123. The needles 137 penetrate the wall of the blood vessel on opposite sides of the puncture and enter the needle receiving lumens 226, if present. The needles 137 should be of sufficient length so that the proximal ends of the needles 137 exit the proximal end of the needle receiving body 220, if present.

Figure 50:
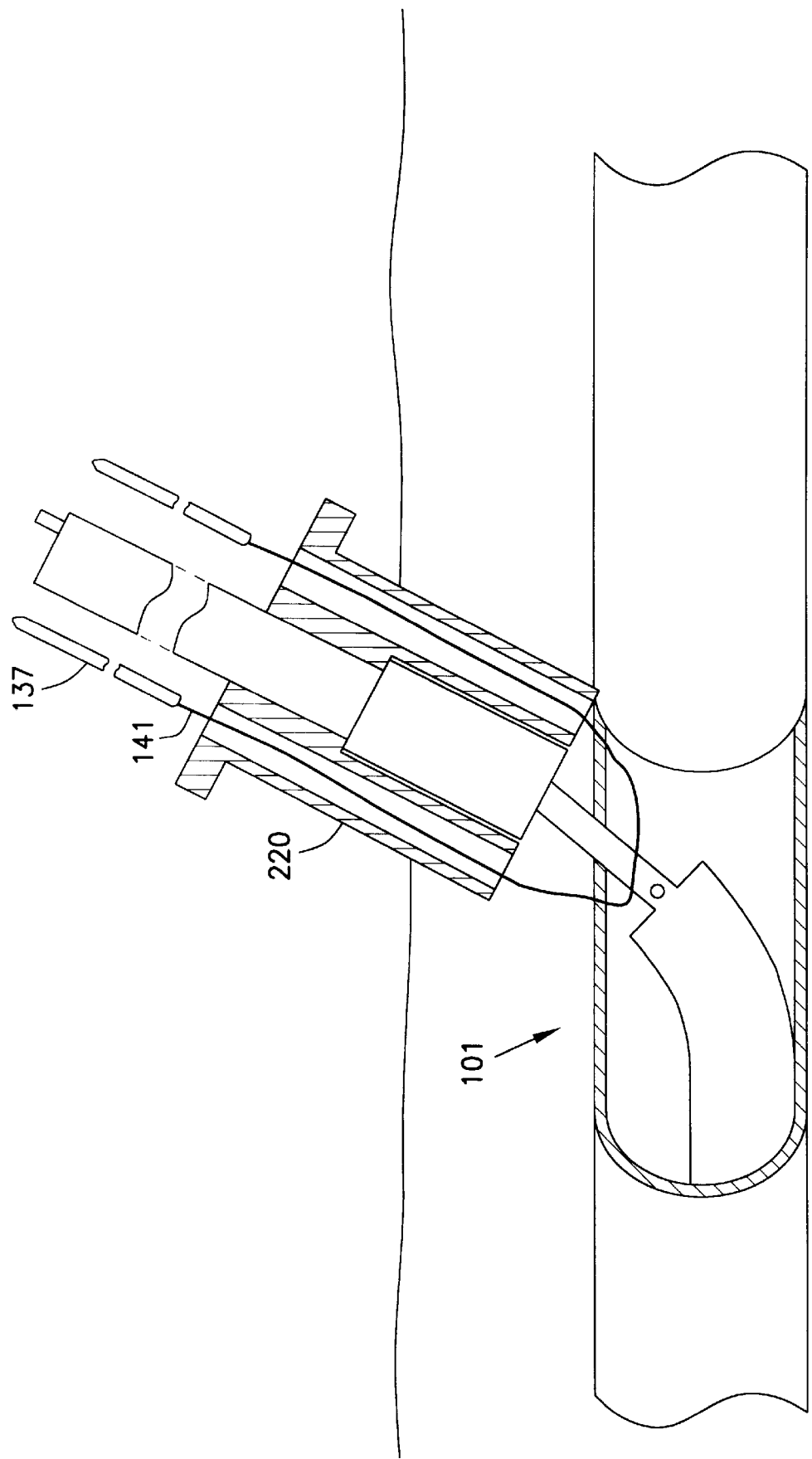
FIG. 50 shows a perspective view of the suture device of FIG. 49 with the pair of puncture needles fully deployed and a length of suture spanning the opening in the anatomical structure.
Figure 51:
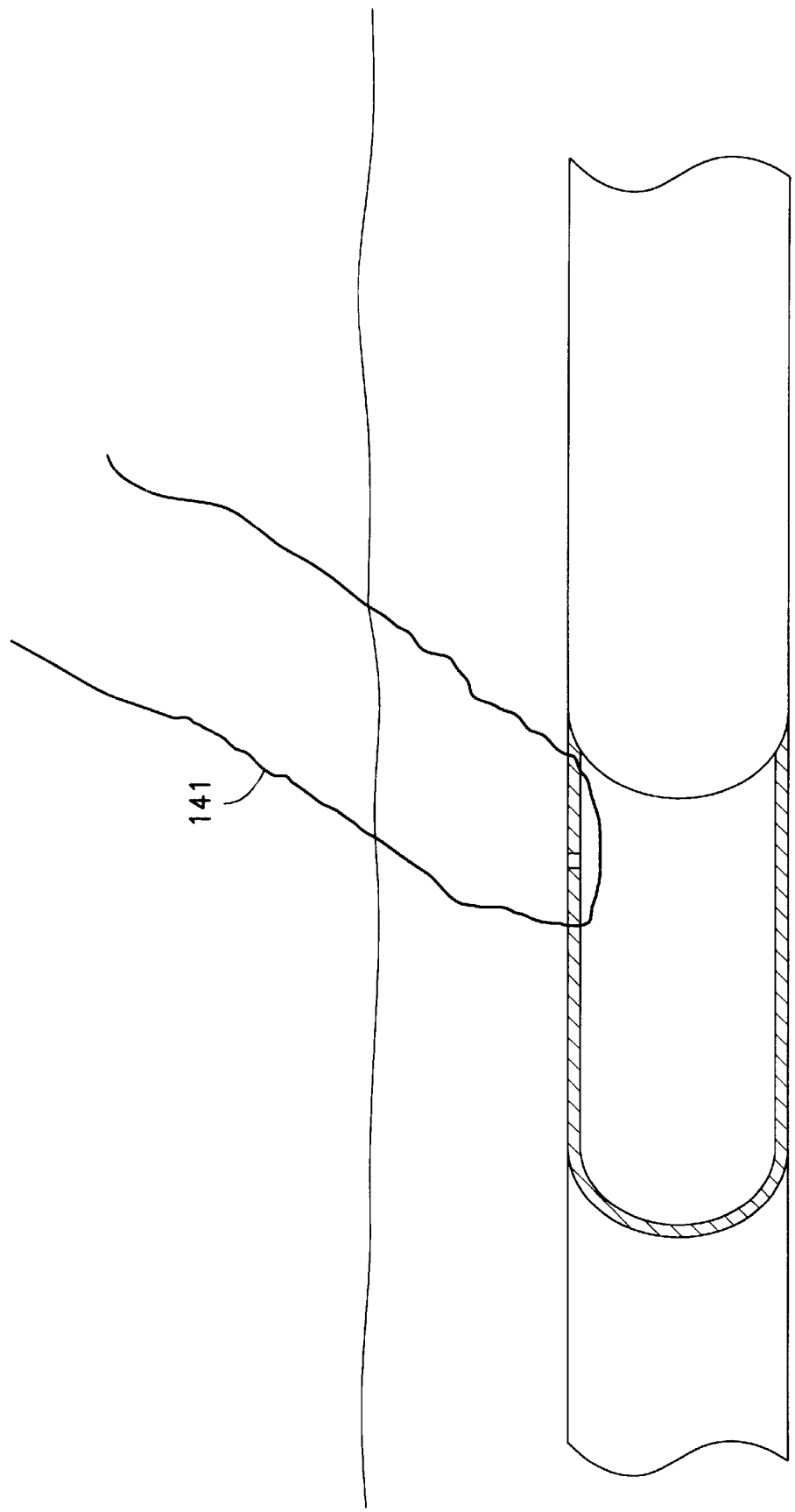
FIG. 51 shows a perspective view of a length of suture after being detached from a suture device according to the present invention.
Figure 52:
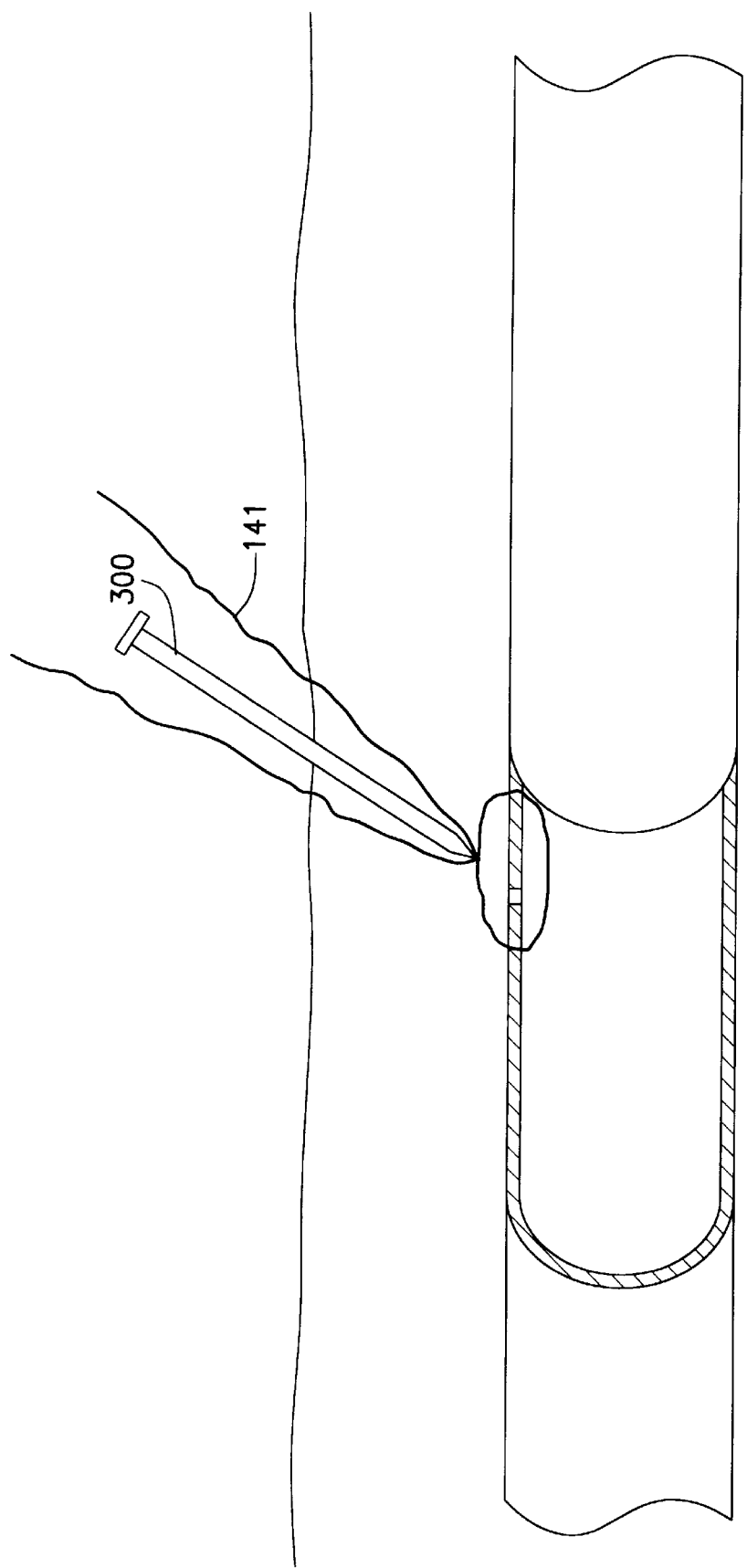
FIG. 52 shows a perspective view of a knot pusher according to the present invention pushing a knotted length of suture.

The operator may then grasp the needles 137 an pull them out of the blood vessel wall and/or needle receiving body 220, thereby pulling the loop 142 of the length of suture 141 back through the suture channel 130 and into the blood vessel, as shown in FIG. 50. The length of suture 141 may then be separated from the needles 137 and withdrawn from the needle receiving body. After the length of suture 141 is knotted, the knot pusher 300 may be used to tighten the knot and the length of suture 141 in general, thereby sealing the puncture. Of course, those skilled in the art will understand that, alternatively, a crimping device 500 as described above may be employed.

Figure 53:
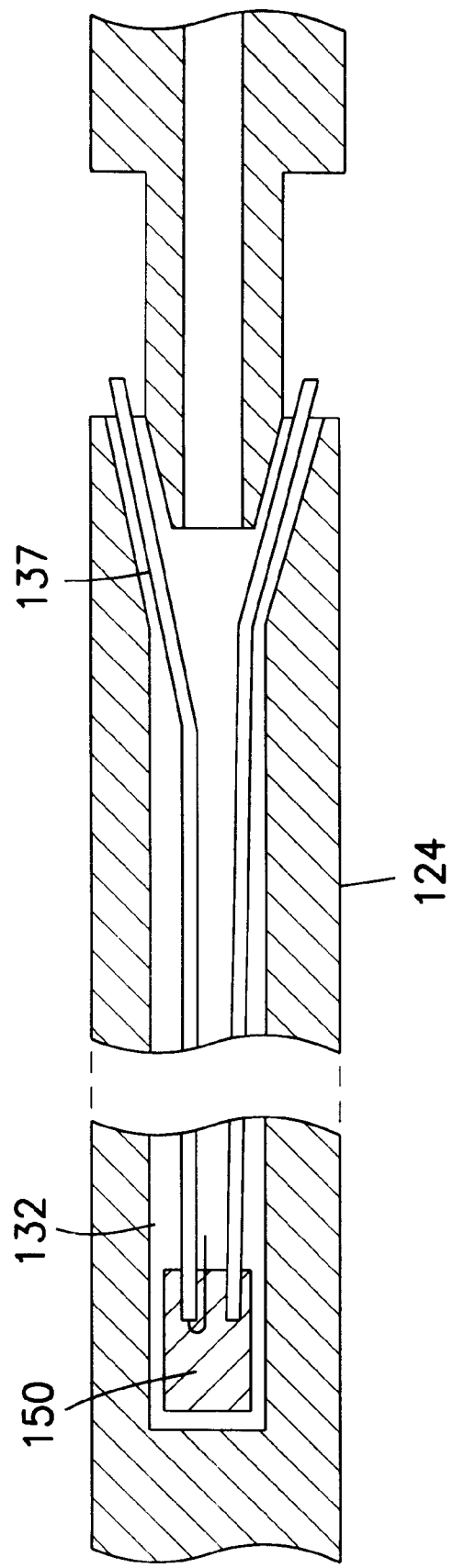
FIG. 53 shows a side view of another embodiment of the suture device according to the present invention.
Figure 54:
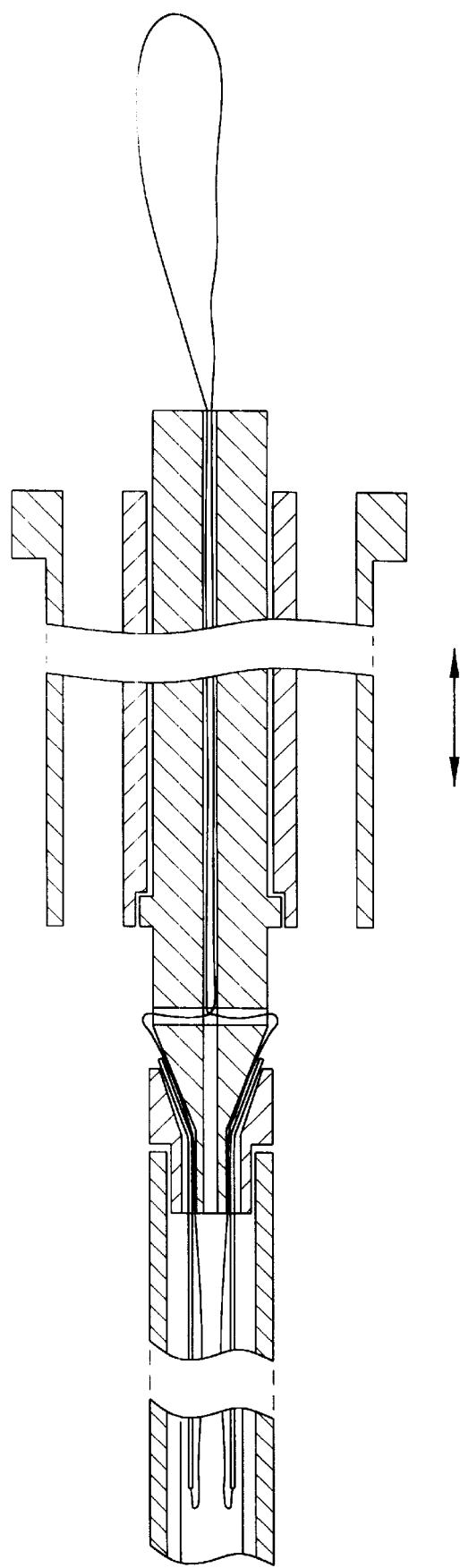
FIG. 54 shows a side view of a suture device according to the present invention including a needle receiving body according to the present invention.

An additional feature of the device 101 according to the present invention is shown in FIG. 53. The needles 137 may be removably implanted in a platform 150 disposed within the needle chamber 132. The platform 150 allows the user to push the needles 137 back into the needle chamber 132 after they have been partially deployed by inserting a rod (not shown) into the suture lumen 130 and the needle chamber 132. The rod can be used to push the platform 150 distally, moving the needles 137 likewise distally, back to their initial position. This feature is useful if, for example, the length of suture 141 breaks prior to complete deployment or one of the needles 137 meets an obstruction.

Figure 55:
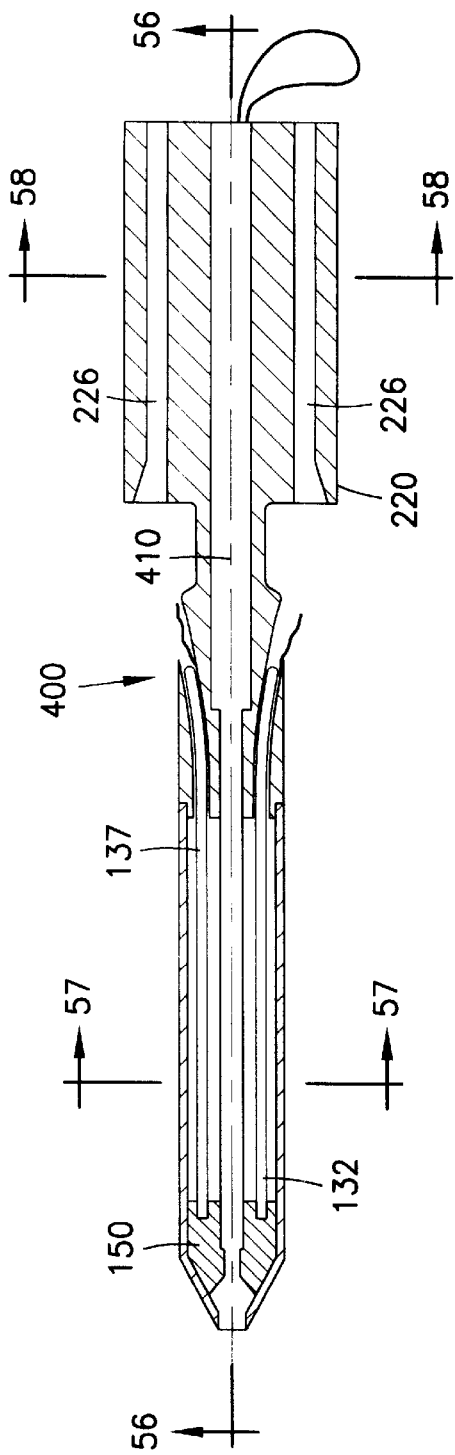
FIG. 55 shows a cross-sectional view of a further exemplary embodiment of a suture device according to the present invention.
Figure 58:
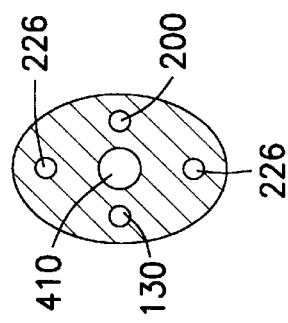
FIG. 58 shows a cross-sectional view of the suture device of FIG. 55 taken along line 58—58 of FIG. 55.

Platform 150 is particularly useful in conjunction with a further embodiment of a suture device according to the present invention, in which the guide wire 44 is utilized to deploy needles 137. As illustrated in FIG. 55, a device 400 according to this embodiment includes a guide lumen 410 extending through the entire length of the device 400. Guide lumen 410 is constructed to receive guide wire 44, and is preferably disposed centrally within device 400, as illustrated in FIG. 58. Device 400 may include other lumens and chambers as described above.

Platform 150 of device 400 is preferably cylindrical in shape, meaning only that platform 150 preferably includes a bore therethrough. It should be understood that the term "cylindrical" therefore includes any configuration having a bore therethrough. Platform 150 may then be located so that the bore is aligned with guide lumen 410. In this manner, guide wire 44 may extend through platform 150.

Guide wire 44 of device 400 includes a fitting 420 coupled to wire 44, "coupled" including any arrangement in which fitting 420 and wire 44 are attached, including adhesive couplings, mechanical couplings, welding, or integral arrangements. Fitting 420 and platform 150 are constructed to selectively engage one another. Any type of engagement mechanism may be employed for this purpose. Preferred engagement mechanisms include internal and external threads or a lug and groove arrangement.

Figure 60:
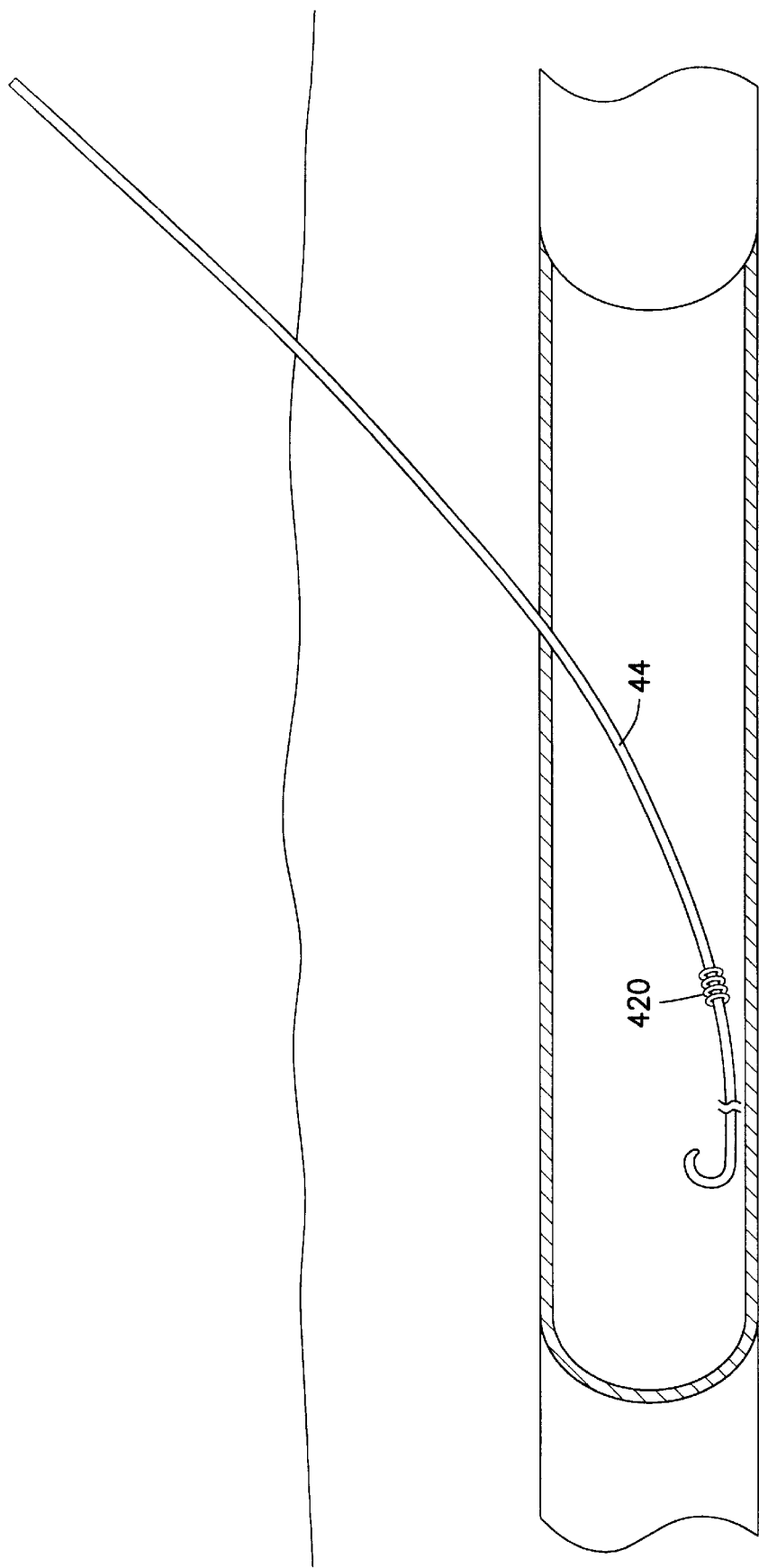
FIG. 60 shows a side view of the guide wire of FIG. 59 inserted into a lumen.
Figure 61:
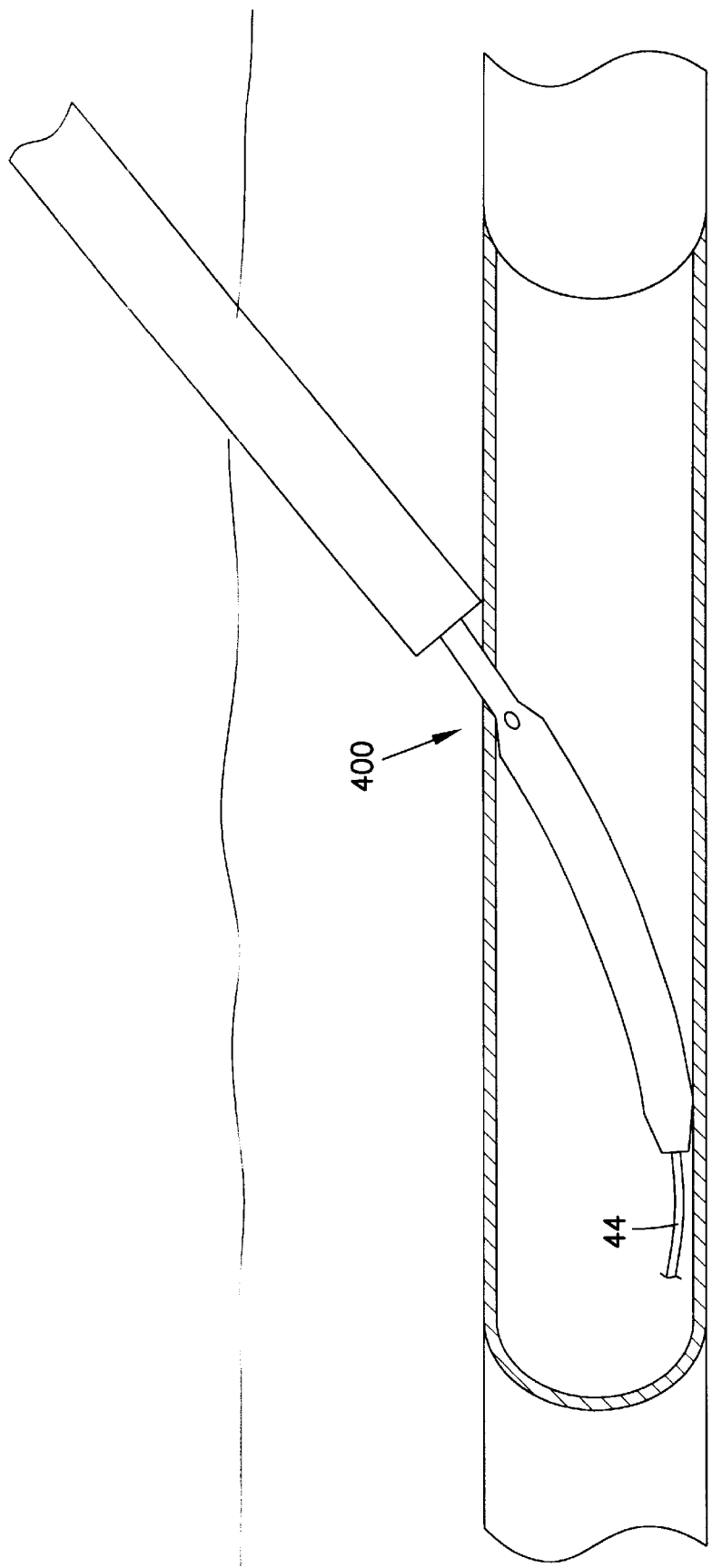
FIG. 61 shows a side view of the device of FIG. 55 inserted over the guide wire of FIG. 60.
Figure 62:
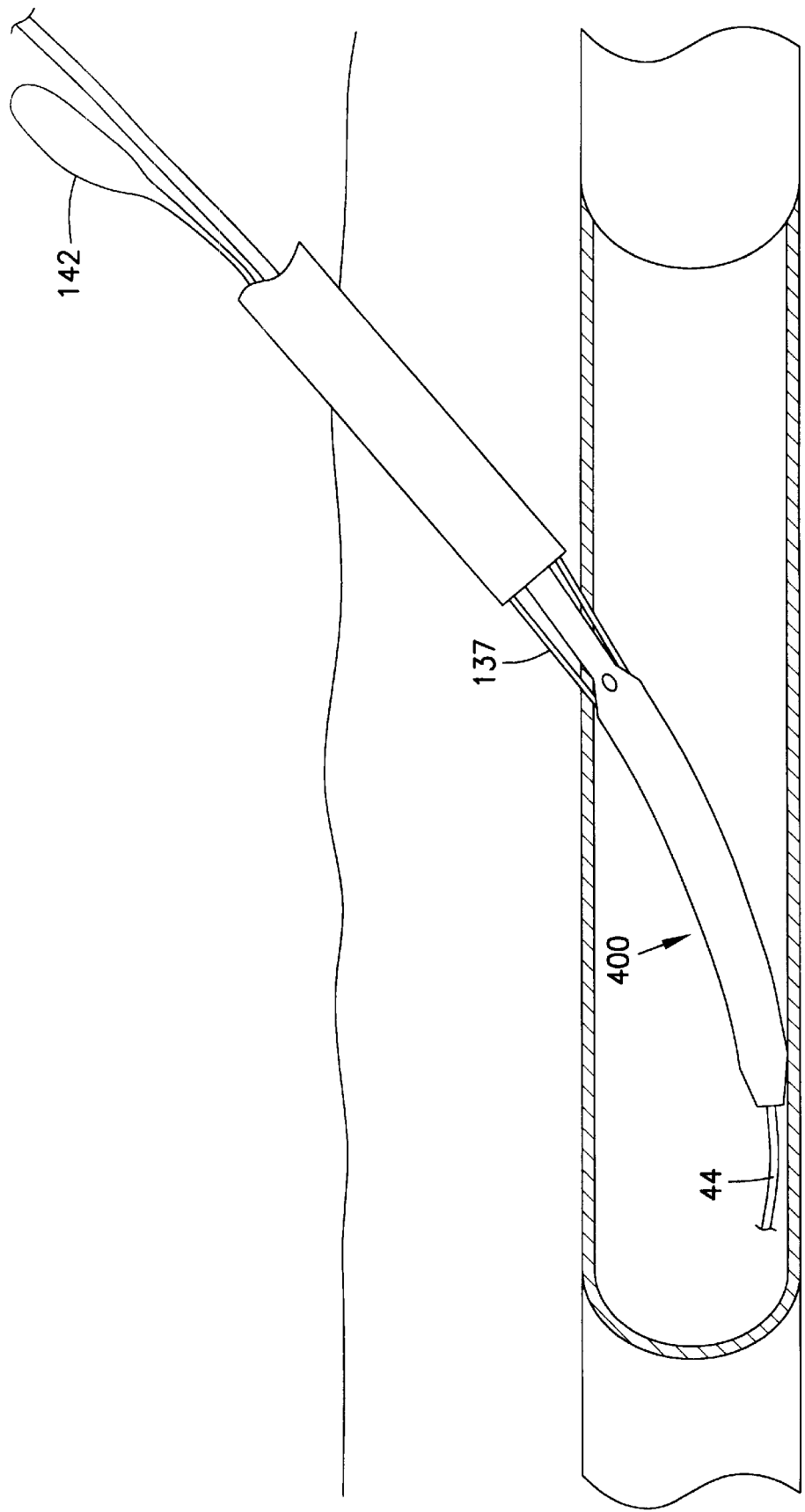
FIG. 62 shows the device of FIG. 61 with an exemplary pair of needles partially deployed.
Figure 63:
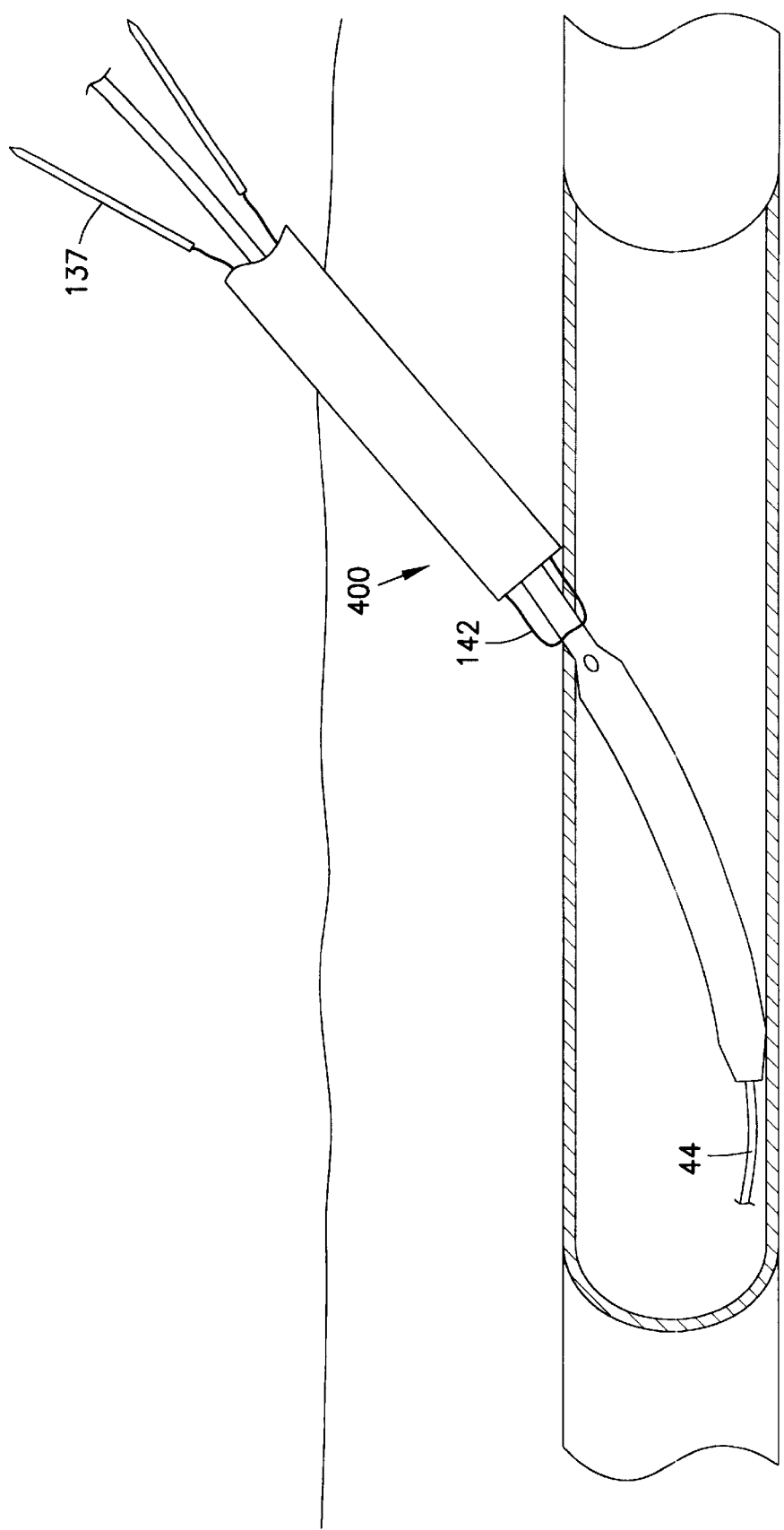
FIG. 63 shows the device of FIG. 61 with the exemplary pair of needles fully deployed.

In practice, guide wire 44 may be inserted into a blood vessel as illustrated in FIG. 60. Device 400 may then be inserted over guide wire 44. Once device 400 has been positioned according to any method, including those described above, guide wire 44 may be withdrawn until fitting 420 and platform 150 are in contact. Guide wire 44 or device 400 (or both) may then be manipulated, e.g. rotated, to engage fitting 420 and platform 150. Guide wire 44 then may be further withdrawn to deploy needles 137, as illustrated in FIGS. 61 to 63. Because this deployment does not require pulling on suture 141, the chance of severing suture 141 is minimized. It should be understood that while the illustrated embodiment includes a suture lumen 130, suture may be completely housed in device 400 if desired.

The embodiment of the device 101 according to the present invention has been described with respect to a single length of suture 141 and a single pair of needles 137. It can be understood, however, that simple modifications (e.g. the addition of more needle channels 123, etc.) allow the deployment of multiple needles simultaneously. Likewise, there are many other variations of the above described embodiments which will be apparent to those skilled in the art. It is understood that these modifications are within the teaching of the present invention which is to be limited only by the claims appended hereto. In addition, although the operation of the various embodiments has been described in regard to the sealing of an opening in the wall of a blood vessel, those skilled in the art will understand that this invention may also be used to seal openings in various internal organs and structures.

What is claimed is:

1. A device for sealing an opening in an anatomical structure within a living body comprising:
   a longitudinal member including a guide lumen and at least one needle lumen;
   a needle at least partly disposed within the needle lumen, the needle being connected at a distal end to a platform; and
   a guide wire having a fitting coupled thereto, the fitting selectively engaging the platform;
   wherein when the longitudinal member is placed over the guide wire and when the fitting and the platform are engaged, movement of the guide wire in a proximal direction causes movement of the needle in the proximal direction and movement of the guide wire in a distal direction causes movement of the needle in the distal direction.

2. The device according to claim 1, the longitudinal member further including a longitudinal needle chamber, the needle chamber having a proximal end, wherein the proximal end of the needle chamber is connected to a distal end of the needle lumens, and wherein the platform and the distal end of the needle are disposed within the needle chamber.

3. The device according to claim 1, comprising a plurality of needles, wherein the at least one needle lumen includes a plurality of needle lumens, each of the plurality of needles being at least partly disposed in a corresponding one of the plurality of needle lumens.

4. The device according to claim 1, wherein the platform is cylindrical in shape, the guide wire selectively extending through the platform.

5. A device for sealing an opening in an anatomical structure within a living body comprising:
   a longitudinal member having a longitudinal guide lumen, including:
      a proximal portion extending from a proximal portion proximal end to a proximal portion distal end;
      a central portion extending from a central portion proximal end coupled to the proximal portion distal end to a central portion distal end; and
      a distal portion extending from a distal portion proximal end coupled to the central portion distal end to a distal portion distal end, wherein a plurality of needle channels extend substantially longitudinally therethrough from the distal portion proximal end;
   a plurality of needles each connected at a distal end to a platform, wherein, in an initial position, each of the needles is at least partly disposed within a respective one of the plurality of needle channels; and
   a guide wire having a fitting coupled thereto, the guide wire being selectively inserted into the guide lumen and the fitting selectively engaging the platform;
   wherein when the fitting and platform are engaged, movement of the guide wire in a proximal direction moves each of the needles from the initial position to a deployed position in which proximal ends of each of the needles suture extend outside the corresponding needle channels.

6. The device according to claim 5, further comprising:
   a longitudinal suture channel extending through the proximal portion of the longitudinal member, and at least part of the central portion of the longitudinal member, the suture channel extending to a suture opening formed in the central portion distal end; and
   a length of suture forming a suture loop and a plurality of suture segments each having a suture end, wherein each of the suture segments extends through the suture lumen, the suture opening, and a respective one of the plurality of needle channels, and wherein each of the suture ends is connected to a distal end of a respective one of the plurality of needles.

7. The device according to claim 5, wherein the distal portion includes a needle chamber extending distally, substantially longitudinally therein from a needle chamber proximal end connected to a distal end of each of the plurality of needle channels, and wherein the platform is located within the needle chamber and, when in the initial position, each of the needles is located substantially within the needle chamber.

8. The device according to claim 5, wherein the distal portion distal end includes a flexible tip.

9. The device according to claim 5, wherein a position indication lumen extends from the proximal portion proximal end through the central portion to a central indication opening located distally of the proximal portion distal end so that, when the device is delivered into the anatomical structure, a body fluid enters the position indication lumen when the device reaches a desired position.

10. The device according to claim 5, further comprising:
    a needle receiving body having a plurality of needle receiving lumens extending therethrough, wherein, when moved between the initial and deployed positions, proximal ends of each of the needles enter respective ones of the needle receiving lumens.

11. The device according to claim 5, wherein the proximal portion includes at least one needle receiving lumen extending therethrough to the proximal portion distal end.

\* \* \* \* \*